(12) United States Patent
Gebhardt et al.

(10) Patent No.: US 11,806,185 B2
(45) Date of Patent: Nov. 7, 2023

(54) COMPUTER-IMPLEMENTED METHOD FOR DETERMINING AT LEAST ONE MAIN ACQUISITION PARAMETER AND METHOD FOR ACQUIRING A MAIN X-RAY IMAGE

(71) Applicant: Siemens Healthcare GmbH, Erlangen (DE)

(72) Inventors: Andre Gebhardt, Markt Erlbach (DE); Sebastian Glawion, Hausen (DE); Thilo Hannemann, Erlangen (DE); Carsten Illenseer, Moehrendorf (DE); Daniel Lerch, Weilersbach (DE); Thomas Pfeiffer, Adelsdorf (DE); Stefan Schaffert, Erlangen (DE); Peter Scheuering, Fuerth (DE); Bastian Schmidt, Eggolsheim (DE); Thomas Weber, Hausen (DE); Wei He, Shanghai (CN); Sven-Martin Sutter, Herzogenaurach (DE); Zhi Ming Yang, Shanghai (CN)

(73) Assignee: Siemens Healthcare GmbH, Erlangen (DE)

(*) Notice: Subject to any disclaimer, the term of this patent is extended or adjusted under 35 U.S.C. 154(b) by 169 days.

(21) Appl. No.: 17/143,270

(22) Filed: Jan. 7, 2021

(65) Prior Publication Data
US 2021/0236081 A1 Aug. 5, 2021

(30) Foreign Application Priority Data
Jan. 30, 2020 (EP) .................................... 20154614

(51) Int. Cl.
*A61B 6/00* (2006.01)
*G06T 7/10* (2017.01)
(Continued)

(52) U.S. Cl.
CPC ................ *A61B 6/542* (2013.01); *A61B 6/06* (2013.01); *A61B 6/4441* (2013.01); *A61B 6/488* (2013.01);
(Continued)

(58) Field of Classification Search
CPC ......... A61B 6/06; A61B 6/4441; A61B 6/488; A61B 6/542; A61B 6/547;
(Continued)

(56) References Cited

U.S. PATENT DOCUMENTS 6,067,341 A * 5/2000 Horiuchi ................ A61B 6/488
378/4
6,404,844 B1 6/2002 Horiuchi et al.
(Continued)

FOREIGN PATENT DOCUMENTS

CA 2616316 A1 2/2007
CN 1360482 A 7/2002
(Continued)

OTHER PUBLICATIONS

Extended European Search Report dated Aug. 10, 2020.

*Primary Examiner* — Dani Fox
(74) *Attorney, Agent, or Firm* — Harness, Dickey & Pierce, P.L.C.

(57) ABSTRACT

A computer-implemented method is for determining at least one main acquisition parameter determining a dose of x-rays to be emitted from an x-ray emitter during image acquisition using an x-ray emitter and an x-ray detector. A first image data of a first preparatory image is evaluated to determine if a repeat condition is fulfilled and/or to determine the main acquisition parameter and/or at least one second preparatory acquisition parameter. The first preparatory image is acquired by the x-ray detector using at least one first preparatory acquisition parameter to control the x-ray emit-
(Continued)

ter. In all cases or when the repeat condition is fulfilled, the main acquisition parameter is determined depending on second image data of a second preparatory image, acquired by the x-ray detector after the first preparatory image while at least one second preparatory acquisition parameter is used to control the x-ray emitter.

18 Claims, 7 Drawing Sheets

(51) Int. Cl.
    *A61B 6/06*     (2006.01)
    *G06T 7/00*     (2017.01)

(52) U.S. Cl.
    CPC ............ *A61B 6/547* (2013.01); *G06T 7/0014* (2013.01); *G06T 7/10* (2017.01); *G06T 2207/10116* (2013.01); *G06T 2207/20081* (2013.01); *G06T 2207/30004* (2013.01); *G06V 2201/03* (2022.01)

(58) Field of Classification Search
    CPC . G06T 2207/10116; G06T 2207/20081; G06T 2207/30004; G06T 7/0014; G06T 7/10; G06V 10/50; G06V 2201/03
    See application file for complete search history.

(56) References Cited

U.S. PATENT DOCUMENTS

| | | |
|---|---|---|
| 2007/0036272 A1 | 2/2007 | Johansson et al. |
| 2015/0359501 A1 | 12/2015 | Eronen et al. |
| 2016/0343128 A1 | 11/2016 | Nitta et al. |
| 2017/0018078 A1 | 1/2017 | Liu et al. |
| 2017/0055927 A1 | 3/2017 | Palma et al. |
| 2018/0211421 A1 | 7/2018 | Wicklein |
| 2018/0329053 A1 | 11/2018 | Qi et al. |
| 2019/0269377 A1 | 9/2019 | Morf et al. |

FOREIGN PATENT DOCUMENTS

| | | |
|---|---|---|
| CN | 203983285 U | 12/2014 |
| CN | 106473762 A | 3/2017 |
| CN | 106572826 A | 4/2017 |
| CN | 109745060 A | 5/2019 |
| CN | 110811651 A | 2/2020 |
| DE | 102005036514 A1 | 2/2007 |
| DE | 102010034680 A1 | 3/2012 |
| EP | 0904732 A1 | 3/1999 |
| WO | WO 2007014105 A2 | 2/2007 |
| WO | WO 2013049818 A1 | 4/2013 |
| WO | WO 2015020981 A2 | 2/2015 |
| WO | WO 2018035814 A1 | 3/2018 |

* cited by examiner

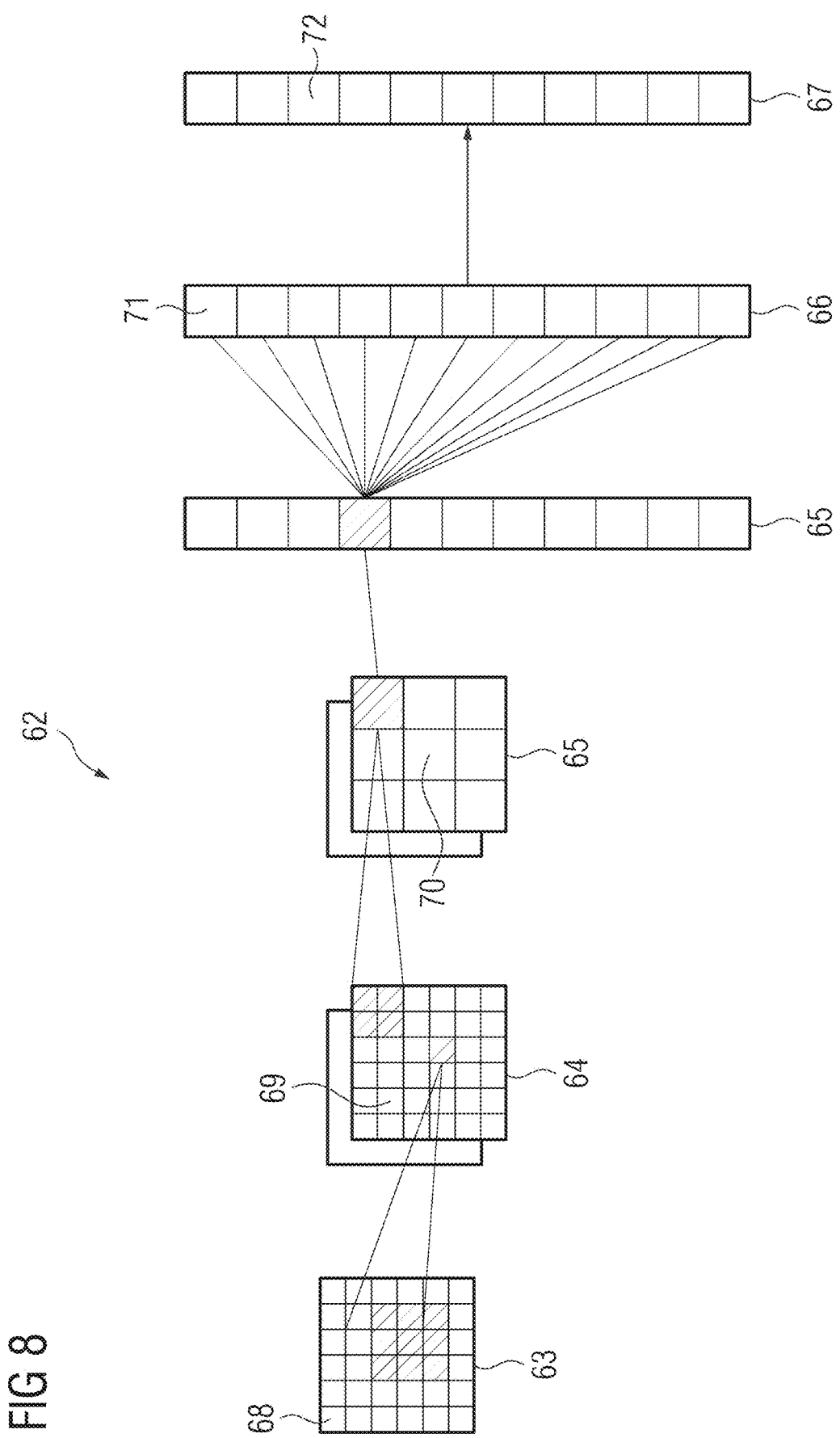

COMPUTER-IMPLEMENTED METHOD FOR DETERMINING AT LEAST ONE MAIN ACQUISITION PARAMETER AND METHOD FOR ACQUIRING A MAIN X-RAY IMAGE

PRIORITY STATEMENT

The present application hereby claims priority under 35 U.S.C. § 119 to European patent application number EP20154614.0 filed Jan. 30, 2020, the entire contents of which are hereby incorporated herein by reference.

FIELD

Example embodiments of the application generally relate to a computer-implemented method for determining at least one main acquisition parameter determining a dose of x-rays to be emitted from an x-ray emitter during a main image acquisition that uses the x-ray emitter and an x-ray detector for imaging an object, especially a patient during a medical image acquisition. Additionally, example embodiments of the application generally relate to a method for acquiring a main x-ray image, a processing unit, a computer program and a computer-readable storage medium.

BACKGROUND

In x-ray imaging, especially in medical x-ray imaging, it is advantageous to use a relatively low dose of x-rays to irradiate an investigated object, especially a patient during a medical image acquisition. Known approaches for limiting the exposure to x-rays are lowering the overall time of exposure, lowering a current provided to an x-ray emitter, e.g. an x-ray tube, and/or limiting the voltage applied to the x-ray emitter.

It is however problematic that an excessive limitation of the used dose might lower the image quality to a degree where a robust evaluation of the acquired image is no longer possible, therefore requiring an additional image acquisition and therefore an additional exposure of the object or patient to a higher dose of x-rays.

It is known to use additional so-called "auto exp. control" (AEC) sensors, e.g. solid-state sensors, placed directly in front of an x-ray detector to determine the patient transmitted dose and stop the x-ray exposure when a given threshold is reached. Alternatively, it would be possible to include fast read-out pixel elements for exposure control among the standard pixel elements in a flat panel detector as e.g. discussed in the document US 2019/0269377 A. Both approaches increase the complexity of the hardware of the system, potentially leading to additional component lifecycle costs. Additional sensor electronics might also increase the necessary dose, since part of the dose might be absorbed by the additional sensors.

In the context of mammography objects with similar properties, namely objects comprising soft tissue, are investigated and x-rays in a limited range of emitter voltages of 23 kV to 35 kV are used. For such cases a different approach is known from the documents DE 10 2010 034 680 A1 and DE 10 2005 036 514 A1. In these documents, a target dose is calculated from a low dose x-ray pre-exposure image of the object under investigation.

SUMMARY

The inventors have discovered that a problem of these approaches is, that they would require additional prior knowledge to provide a robust prediction of the required dose for the final image when used in more general use cases. Even in the context of mammography, where the properties of the investigated objects do not vary widely, the cited documents use additional information concerning the thickness of the compressed breast or other prior knowledge. The inventors have discovered that it is therefore not easily possible to transfer these approaches to more general use cases, where different areas of a patient might be imaged.

At least one embodiment of the present invention therefore provides a method for determining at least one main acquisition parameter controlling a dose of x-rays to be emitted from an x-ray emitter during a main image acquisition that allows for a robust determination of this parameter, even when a wide variability of the imaged objects is expected and/or there is no or only limited prior knowledge about the object.

At least one embodiment of the present invention therefore provides a computer-implemented method for determining at least one main acquisition parameter determining a dose of x-rays to be emitted from an x-ray emitter during a main image acquisition that uses the x-ray emitter and an x-ray detector for imaging an object, especially a patient during a medical image acquisition.

At least one embodiment of the present invention therefore provides a computer-implemented method for determining at least one main acquisition parameter determining a dose of x-rays to be emitted from an x-ray emitter during a main image acquisition using the x-ray emitter and an x-ray detector for imaging an object, the computer-implemented method comprising:

evaluating a first image data of a first preparatory image to at least one of
  determine whether or not a repeat condition is fulfilled
  determine at least one of the main acquisition parameter and
  determine at least one second preparatory acquisition parameter, the first preparatory image being an image acquired by the x-ray detector using at least one first preparatory acquisition parameter to control the x-ray emitter; and
determining, at least one of in all cases or only when the repeat condition is fulfilled, the main acquisition parameter depending on second image data of a second preparatory image, acquired by the x-ray detector after the first preparatory image while at least one second preparatory acquisition parameter is used to control the x-ray emitter.

At least one embodiment of the invention also concerns a training system comprising a first training interface, configured for receiving input training data, e.g. the input data discussed above, a second interface, configured for receiving output training data, e.g. the desired values for the respective acquisition parameter or parameters discussed above, wherein the input training data is related to the output training data, a training computation unit, configured for training an algorithm based on the input training data and the output training data, and a third training interface, configured for providing the trained algorithm.

Additionally, at least one embodiment of the invention concerns a computer program comprising instructions which, when the programs is executed by a computer, cause the computer to carry out the training of the algorithm. At least one embodiment of the invention also concerns a computer-readable medium comprising the instructions of the previously discussed computer program.

At least one embodiment of the invention also concerns the trained algorithm or any parameter set that parametrises a given algorithm to provide such a trained algorithm. A trained algorithm and/or the parameter set can especially be provided by the previously discussed method for training the algorithm and/or by the previously discussed training system. Therefore the invention also concerns a computer-readably storage medium comprising such a parameter set or trained algorithm.

At least one embodiment of the invention also concerns a method for acquiring a main x-ray image during a main image acquisition that uses an x-ray emitter and an x-ray detector for imaging on object, especially a patient during a medical image acquisition, wherein a first preparatory image is acquired by the x-ray detector using at least one first preparatory acquisition parameter to control the x-ray emitter, wherein a second preparatory image is acquired by the x-ray detector using at least one second preparatory acquisition parameter to control the x-ray emitter, in all cases or when a repeat condition is fulfilled, and wherein the main x-ray image is acquired using a main acquisition parameter that controls the x-ray emitter during the main image acquisition to determine a dose of x-rays to be emitted from the x-ray emitter during the main image acquisition, wherein first image data of the first preparatory image is evaluated to determine if the repeat condition is fulfilled and/or to determine the main acquisition parameter and/or the second preparatory acquisition parameter, and wherein the main acquisition parameter is determined depending on second image data of the second preparatory image in all cases or when the repeat condition is fulfilled.

At least one embodiment of the invention also concerns a method for acquiring a main x-ray image during a main image acquisition using an x-ray emitter and an x-ray detector for imaging an object, comprising:

acquiring a first preparatory image via the x-ray detector, using at least one first preparatory acquisition parameter to control the x-ray emitter;

acquiring a second preparatory image via the x-ray detector, using at least one second preparatory acquisition parameter to control the x-ray emitter, at least one of in all cases or when a repeat condition is fulfilled; and acquiring the main x-ray image using a main acquisition parameter, that controls the x-ray emitter during the main image acquisition to determine a dose of x-rays to be emitted from the x-ray emitter during the main image acquisition;

wherein first image data of the first preparatory image is evaluated at least one of to determine fulfilment of the repeat condition and to determine at least one of the main acquisition parameter and the second preparatory acquisition parameter, and wherein the main acquisition parameter is determined depending on second image data of the second preparatory image, at least one of in all cases or when the repeat condition is fulfilled.

Besides the inventive methods, at least one embodiment of the invention also concerns a processing unit, especially a processing unit of a medical imaging device, configured to perform at least one of the methods according to at least one embodiment of the present invention.

Additionally, at least one embodiment of the invention concerns an imaging device, especially an imaging device for medical imaging, comprising such a processing unit. The imaging device can comprise the x-ray emitter and the x-ray detector and the processing unit can optionally be configured to control the imaging. The processing unit can especially be configured to control the main image acquisition according to the at least one main acquisition parameter, to control the acquisition of the first preparatory image according to the at least one first preparatory acquisition parameter and/or to control the acquisition of the second preparatory image according to the at least one second preparatory acquisition parameter.

At least one embodiment of the invention also concerns a computer program that can be directly loaded into a memory unit of a processing unit, especially a processing unit of a medical imaging device, the computer program comprising instructions for performing the steps of at least of the methods according to at least one embodiment of the present invention when the program is executed in the processing unit.

At least one embodiment of the invention also concerns a computer-readable storage medium containing electronically readable instructions comprising the computer program according to at least one embodiment of the present invention.

BRIEF DESCRIPTION OF THE DRAWINGS

Other objects and features of the present invention will become apparent from the following detailed description considered in conjunction with the accompanying drawings. The drawings, however, are only principle sketches design solely for the purpose of illustration and do not limit the invention. The drawings show.

DETAILED DESCRIPTION OF THE EXAMPLE EMBODIMENTS

Figure 1:
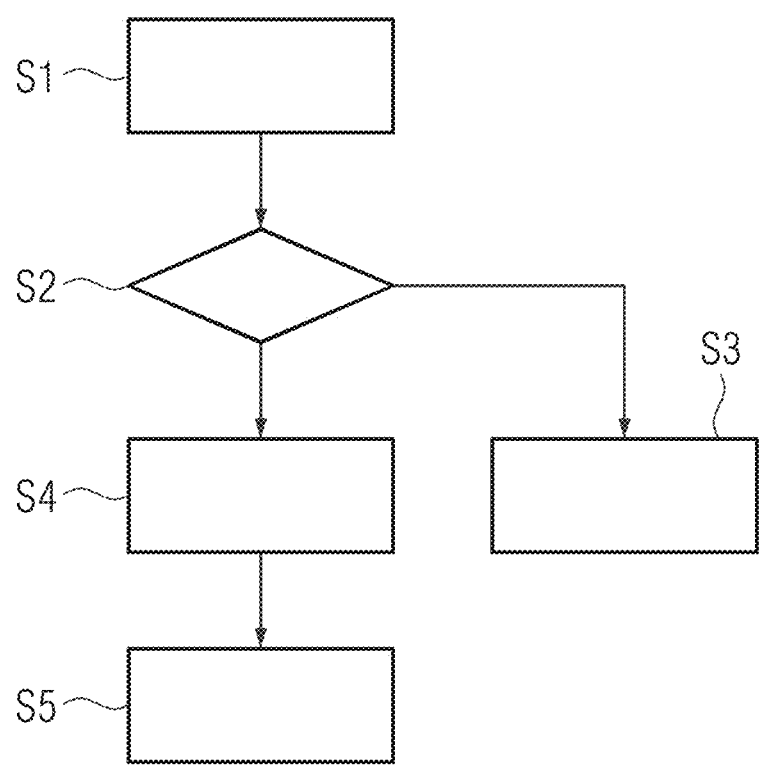
FIG. 1 shows a flow chart of an example embodiment of the computer-implemented method for determining at least one main acquisition parameter according to the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention therefore provides a method for determining at least one main acquisition parameter controlling a dose of x-rays to be emitted from an x-ray emitter during a main image acquisition that allows for a robust determination of this parameter, even when a wide variability of the imaged objects is expected and/or there is no or only limited prior knowledge about the object.

At least one embodiment of the present invention therefore provides a computer-implemented method for determining at least one main acquisition parameter determining a dose of x-rays to be emitted from an x-ray emitter during a main image acquisition that uses the x-ray emitter and an x-ray detector for imaging an object, especially a patient during a medical image acquisition.

First image data of a first preparatory image is evaluated to determine if a repeat condition is fulfilled and/or to determine the main acquisition parameter and/or at least one second preparatory acquisition parameter, wherein the first preparatory image is an image acquired by the x-ray detector using at least one first preparatory acquisition parameter to control the x-ray emitter.

Either in all cases or only when the repeat condition is fulfilled the main acquisition parameter is determined depending on second image data of a second preparatory image, that is an image acquired by the x-ray detector after the first preparatory image while the or at least one second preparatory acquisition parameter is used to control the x-ray emitter.

At least one embodiment of the present invention is based on the idea that, in all cases or at least in the case when a repeat condition is fulfilled, not only one but two or even more preparatory images are evaluated to determine the main acquisition parameter. This allows for the gathering of additional information concerning the behaviour of the used emitter and detector when the investigated object is present. For simplicity's sake these features are discussed in detail mainly for the use of two preparatory images. If more than two preparatory images are used, the first and second preparatory image can be any pair of the preparatory images, but preferably a pair of successively acquired preparatory images can be used as first and second preparatory images. It is e.g. possible to evaluate the respective image data of each preparatory image or at least some of the preparatory images to check if a repeat condition is fulfilled by this image data and only acquire or evaluate a further preparatory image when the repeat condition is fulfilled. When the repeat condition is not fulfilled for a certain preparatory image, the main acquisition parameter can e.g. be determined based on the preparatory image for which the repeat condition was not fulfilled and/or based on further previously evaluated and/or acquired preparatory images.

If multiple prior images are acquired and/or evaluated, the main acquisition parameter can depend on the image data of all or some of these preparatory images. Additionally or alternatively the respective acquisition parameter used to control the x-ray emitter during the acquisition of the respective preparatory image can depend on the image data of at least one previously acquired and/or evaluated preparatory image.

If multiple preparatory images are acquired, it is also possible to average or sum the image data of at least some of the preparatory images to generate an intermediate image. The determination of the fulfilment of the repeat condition and/or the main acquisition parameter and/or a respective preparatory acquisition parameter for the acquisition of a further preparatory image can then depend on the image data of the intermediate image. It is e.g. possible to determine an intermediate image based on the first preparatory image and a further preparatory image and then determine the second preparatory acquisition parameter based on the image data of the intermediate image. It is also possible to e.g. sum the first and second preparatory image and to determine the main acquisition parameter based on this sum. In this case the main acquisition parameter depends on the image data of the first and second preparatory image.

The main image acquisition can especially be an acquisition of a single x-ray image or of a limited number, e.g. less than 10 or 100, x-ray images. In acquisitions that acquire a large number of x-ray images in quick succession, e.g. in fluoroscopy, different approaches to dose control might be advantageous.

The potential acquisition of two or more separate images especially allows for a very low x-ray dose to be used for acquiring the first preparatory image. In imaging situations where a rather low dose is sufficient for the main image acquisition, it can be recognized from the first preparatory image that the acquisition of the second preparatory image might not be necessary to determine the main acquisition parameter. In this case the repeat condition might not be fulfilled and only one preparatory image acquisition might be used.

On the other hand, the first preparatory image can be used to modify the acquisition of the second preparatory image, e.g. to choose the at least one second preparatory acquisition parameter in such a way that a higher emitted dose can be chosen for the acquisition of the second preparatory image as required. Additionally or alternatively an emitter voltage can be changed for the second preparatory image based on the first image data, e.g. to achieve a lower x-ray absorption by the object. If more than two preparatory images are used, this teaching can apply to all pairs or at least one pair of successively acquired preparatory images.

As will be discussed in more detail below, the first preparatory image can be acquired at a very low dosage, therefore limiting the unavoidable preparatory image dose. The very low dosage required for the first preparatory image also allows for a very fast exposure that can even be performed while the x-ray emitter, e.g. an x-ray tube, is still prepared for the main acquisition, e.g. by spinning up an anode and/or heating a cathode. The inventive approach can therefore be integrated into a normal image acquisition workflow with no or miniscule additional time while still ensuring a robust exposure control during the main image acquisition while keeping the applied dose low.

At least one embodiment of the inventive method can be implemented in different ways. In a preferred approach at least some of the first image data or data derived from the first image data is processed as input by an algorithm implementing the evaluation of the repeat condition. If the repeat condition is not fulfilled, at least part of the first image data or data derived from this data can be used as an input of an algorithm used for determining the main acquisition parameter. If the repeat condition is fulfilled, at least part of the second image data or data derived from the second image data can be used as input data of the algorithm or a further algorithm for determining the main acquisition parameter. In an advantageous embodiment, the acquisition of the second image is only performed when the repeat condition is fulfilled. The discussed procedure could e.g. be repeated to evaluate and/or acquire further preparatory images, until the repeat condition is no longer fulfilled or some other termination criterion stops the evaluation and/or acquisition.

Both the algorithm or algorithms for determining the main acquisition parameter and the algorithm for evaluating the repeat condition can optionally depend on additional input data, e.g. patient data, image data from a camera or 3D data from a 3D depth camera used to capture an image of the object etc.

It is also possible to determine the main acquisition parameter depending on the first and second image data together. This might be advantageous, since the first image data might still improve the quality of the determination of the acquisition parameter, even if it is not sufficient by itself to determine this parameter.

In another embodiment of the inventive method, the use of the second image data from a second preparatory image acquisition is obligatory, i.e. when a repeat condition is not used, and the second image data is always used as input data for an algorithm used to determine the main acquisition parameter. In the simplest case, the acquisition of the first image data and the second image data can be essentially independent of each other, e.g. by using independent and/or different exposure settings for the acquisitions, and the algorithm used to determine the main acquisition parameter can depend on both sets of data.

The preparatory images can not only be used for the determination of the main acquisition parameter. As will be discussed in more detail below it can be advantageous to use these images while evaluating the image acquired during the main image acquisition, e.g. to support a segmentation or a classification of an image content of this image.

The x-ray emitter can be an x-ray tube. It can however also comprise additional components that can influence the dose, e.g. a shutter or collimator, that can be controlled to modify the dose irradiated onto the object.

Advantageously, the second preparatory acquisition parameter used for the acquisition of the second preparatory image differs from the first preparatory acquisition parameter used to control the x-ray emitter during the acquisition of the first preparatory image. E.g. a higher dose of emitted x-rays can be used during the acquisition of the second preparatory image, e.g. by using a longer exposure time and/or a higher emitter current. Alternatively or additionally an emitter voltage can be changed, especially increased, to potentially lower the x-ray absorption by the object and therefore the absorbed dose.

In this document, a multitude of parameters that are determined in dependence of other parameters are mentioned. This dependence can be implemented by using an algorithm that outputs the output parameter or parameters and uses the parameter or parameters, on which the output parameter or parameters depend, as inputs. One way of implementing such an algorithm is by using a look-up table. It is also possible to implement such algorithms as analytical functions, as complex programs, etc. In some cases, it might also be advantageous to use machine learning to train an algorithm to calculate the mentioned parameters.

The main acquisition parameter or parameters can e.g. describe an emitter voltage and/or an emitter current and/or an emitter charge used during the main image acquisition and/or an x-ray dose emitted from the x-ray emitter and/or absorbed by the object during the main image acquisition.

The first preparatory image can be an image acquired using a first emitter voltage of less than 65 kV and/or a first emitter current of less than 15 mA and/or a first exposure time of less than 75 ms and/or a first emitter charge of less than 750 µAs and/or a first rotational speed of an anode of the x-ray emitter of less than 10 Hz as first preparatory acquisition parameters. In an example, an emitter voltage of e.g. 40 kV can be used. The emitter current can e.g. be 10 mA and the exposure time can e.g. be between 10 ms and 50 ms. The given emitter current and exposure time result in an emitter charge between 100 µAs and 500 µAs. The given parameter values are example and can e.g. vary by up to 20% or up to 50% from the given values.

Concerning the exposure time, it can be advantageous to use a relatively long exposure time, e.g. at least 10 ms or at least 20 ms, to ensure defined conditions of the emitter voltage and current and to eliminate time-dependent loss of emitter voltage due to the cabling. A too short exposure time might lead to errors in the expected imaging conditions and therefore errors when extrapolating the image acquisition to determine the main acquisition parameter and/or the second preparatory acquisition parameter and/or when evaluating the fulfilment of the repeat condition.

The discussed parameter ranges especially allow for an acquisition of the first preparatory image while the x-ray emitter, e.g. an x-ray tube, is not yet fully prepared for the main image acquisition. The low required emitter currents can e.g. be already provided before a cathode of the x-ray emitter is fully heated. Since relatively low currents and voltages are used, there is also a limited heating of the anode. It can therefore be possible to perform the acquisition of the first preparatory image before a rotating anode reaches its full operational speed. E.g. the first preparatory image can be acquired while the anode is standing still, at least at the beginning of the image acquisition, or is rotating at a rather low speed.

The emitter charge, e.g. a tube charge, is typically defined as the product of the emitter current and the exposure time. If a variable current should be used for the exposure, the emitter charge can be calculated by integrating the emitter current over the exposure time.

The first preparatory acquisition parameter or at least one of the first preparatory acquisition parameters can describe a first x-ray dose emitted from the x-ray emitter and/or absorbed by the object during the acquisition of the first preparatory image and/or a first emitter voltage and/or a first emitter current and/or a first exposure time and/or a first emitter charge and/or a first rotational speed of the or an anode of the x-ray emitter used during the acquisition of the first preparatory image.

The second preparatory acquisition parameter or at least one of the second preparatory acquisition parameters can describe a second x-ray dose emitted from the x-ray emitter and/or absorbed by the object during the acquisition of the second preparatory image and/or a second emitter voltage and/or a second emitter current and/or a second exposure time and/or a second emitter charge and/or a second rotational speed of the anode of the x-ray emitter used during the acquisition of the second preparatory image.

The first and second preparatory image can be images acquired in such a way that the second x-ray dose is larger than the first x-ray dose and/or that the second emitter voltage is larger than the first emitter voltage and/or that the second emitter current is larger than the first emitter current and/or that the second exposure time is larger than the first exposure time and/or that the second emitter charge is larger than the first emitter charge and/or that the second rotational speed is larger than the first rotational speed.

Increasing the emitter current, the exposure time or the resulting emitter charge for the acquisition of the second preparatory image tends to improve the image quality of the second preparatory image over the image quality of the first preparatory image. This approach might especially be advantageous when the second preparatory image is only acquired when a repeat condition is fulfilled. In cases in which the image quality of the first preparatory image is already sufficient, the determination of the main acquisition parameter can be achieved with a very low emitted x-ray dose. If the quality is however not sufficient, a second preparatory image with an improved quality can be acquired to allow for a more robust determination of the main acquisition parameter.

As previously mentioned, the first preparatory image and preferably also the second preparatory image can be acquired while the emitter is not quite ready for the main image acquisition, e.g. while the anode is still spinning up and/or while the cathode is still not at its optimum temperature. At relatively low cathode temperatures only a limited emitter current can be provided. It is therefore e.g. possible to acquire the first preparatory image at a relatively low cathode temperature and therefore with a relatively low emitter current and increase the cathode temperature during the first preparatory image acquisition or between the first and the second preparatory image acquisition, therefore allowing for larger emitter current during the second preparatory image acquisition. Similarly, the lower rotational speed with an anode might require limiting the power dissipated on the anode during the first and/or second preparatory image acquisition, therefore limiting the usable emitter voltage and/or emitter current.

It was found to be advantageous to use a second emitter charge that is approximately ten times larger than the first emitter charge. In certain cases it might, however, also be advantageous to use a second emitter charge, that is at least three times, at least five times or at least 15 times as large as the first emitter charge. The emitter charge can be increased by increasing the emitter current and/or the exposure time.

As already discussed, more than two preparatory images can be used and especially acquired. As an example, the use of a third preparatory image will be discussed below. The same discussion applies to further preparatory images, e.g. a fourth, fifth, etc., preparatory image. In this case any pair of previously acquired preparatory images, especially a pair of successively acquired preparatory images, can be used instead of the first and second preparatory image to determine if the respective repeat condition to acquire and/or evaluate the respective further preparatory image is fulfilled and/or to determine further preparatory acquisition parameters for that further preparatory image acquisition etc.

The discussed changes of the acquisition parameters between the acquisition of the first and second preparatory image can be continued for the acquisition of further preparatory images. E.g. the emitted and/or absorbed dose and/or the emitter voltage and/or emitter current and/or exposure time and/or emitter charge and/or rotational speed of the anode can be successively increased with each preparatory image acquisition. This is however optional and not necessary or desirable in all cases.

The second image data can be evaluated to determine if a further repeat condition is fulfilled, wherein the main acquisition parameter is determined depending on the third image data of a third preparatory image when the further repeat condition is fulfilled, wherein the third preparatory image is an image acquired by the x-ray detector after the second preparatory image while at least one third preparatory acquisition parameter is used to control the x-ray emitter. It can be advantageous to further increase the emitter voltage and/or the emitter current and/or the exposure time and/or the emitter charge and/or the rotational speed of the anode beyond the values used for the second preparatory image acquisition. E.g. a third emitter charge used for the third preparatory image acquisition can be ten times larger than the second emitter charge.

While the use of the first and second preparatory image is typically sufficient for a robust determination of the main acquisition parameter, allowing for a third preparatory image acquisition when necessary can be advantageous to allow for a robust determination of the main acquisition parameter for even more use cases. E.g. when imaging an obese patient or areas mainly containing strongly x-ray absorbing materials, e.g. bones, a robust determination of the main acquisition parameter using only two preparatory image acquisitions might require a relatively high x-ray dose for these two acquisitions. It can therefore be advantageous to use a lower dose for the first and second preparatory image acquisition and to allow for the third image acquisition when necessary.

The fulfilment of the repeat condition and/or the main acquisition parameter and/or the second preparatory parameter can depend on at least one grey value determined from a respective segment of the first preparatory image, wherein preferably the position of the respective segment in the first preparatory image is fixed or selected by a user or determined by a segmentation algorithm, and/or on a histogram of the first image data or of part of the first image data and/or on a signal difference to noise ratio for the first image data or part of the first image data.

The fulfilment of the further repeat condition and/or the main acquisition parameter and/or a third preparatory acquisition parameter used to acquire the third preparatory image can depend on at least one grey value determined from a respective segment of the second preparatory image, wherein preferably the position of the respective segment in the second preparatory image is fixed or selected by a user or determined by a segmentation algorithm, and/or on a histogram of the second image data or part of the second image data and/or on a signal difference to noise ratio for the second image data or part of the second image data.

If a third preparatory image is used the main acquisition parameter can depend on at least one grey value determined from a respective segment of the third preparatory image, wherein preferably the position of the respective segment in the third preparator image is fixed or selected by a user or determined by a segmentation algorithm, and/or on a histogram of the third image data or of part of the third image data and/or on a signal difference to noise ratio for the third image data or part of the third image data.

In a simple case, a fixed or a user-defined segmentation can be used to achieve a similar behaviour as the sensors of well-known automatic exposure controllers. As already discussed in the introduction, such automatic exposure controllers measure intensities in certain fixed areas of the x-ray detector. This can be emulated by segmenting fixed or user selectable areas in the respective preparatory image and then e.g. determining an average or median grey value for this segment. Alternatively, or additionally, it might also be advantageous to segment known structures in the respective image, e.g. certain organs, bones, etc. To determine grey values for these structures.

It can be sufficient to determine a single grey value and determine the fulfilment of the and/or the further repeat condition, the main acquisition parameter and/or the second and/or third preparatory acquisition parameter from this single grey value. This can however lead to errors, if an offset is present in the grey values of the respective image.

It can therefore be advantageous to determine grey values from at least two segments and then e.g. use the difference of these grey values to determine the mentioned parameters or the fulfilment of the mentioned conditions. For example, the emitter charge used for a following acquisition, especially the main acquisition, can be proportional to the quotient of a target value for a grey value and the grey value determined from a segment of the respective image. Alternatively, this emitter charge can be proportional to the quotient of a target value for a difference between two grey values and the difference between two grey values of different segments in the respective image.

Segmenting specific regions of interest in a preparatory image acquired at a relatively low dose can be challenging. To improve the robustness of the segmentation, mainly two approaches can be used. As a first approach, binning can be used to combine multiple detector elements of the x-ray detector into a superpixel. This can be achieved on the detector itself or the superpixel generation can be performed once the image is acquired, e.g. by averaging or adding all grey values of individual pixels within the superpixel to generate an image at a lower resolution. Such binning noticeably reduces noise at a lower x-ray dose and can therefore improve segmentation and other processing required for the determination of the main acquisition parameter. It also advantageously reduces the computational resources required to determine the main acquisition parameter.

A second approach for improving the segmentation can be the use of additional data, especially the use of an additional input image, that can e.g. be acquired by an optical, an infrared and/or a THz-camera. From such an image a body profile can be generated that can be used for the segmentation of the object when the coordinate system of the camera is registered or can be registered to the coordinate system of the x-ray detector.

Since the purpose of the previously mentioned segmentation in the method for determining the main acquisition parameters is mainly to determine typical grey values or contrasts between typical grey values in the image, it can also be advantageous to use a histogram-controlled grey value search. A histogram for the individual pixels of the respective image or of superpixels, when binning is used as discussed above, can be used to identify clusters of similar grey values. Each of these clusters can then be associated with a specific absorption behaviour and it is e.g. possible to select one or multiple of these clusters and determine typical grey values for the clusters, e.g. average grey values or median grey values, that can then be processed as discussed above.

It is often desirable to not purely control a dose based on the achieved grey values or a contrast, but to also take image noise into consideration. It can therefore be advantageous to calculate a signal difference to noise ratio for the image data of the respective image or for part of that image data, e.g. for a specific segment of the image. Approaches for determining a signal difference to noise ratios in medical imaging are well-known in the prior art and shall therefore not be discussed in detail. The determined signal difference to noise ratio can directly be used to determine the respective parameters or to determine if the or the further repeat condition is fulfilled. A dose or emitter charge for a later image acquisition, e.g. for the main image acquisition, can e.g. be proportional to the quotient of a desired value for the signal difference to noise ration and the determined signal difference to noise ratio.

The determination of the discussed parameters and/or the fulfilment of the or the further repeat condition can also be performed by an algorithm that is trained by machine learning. The algorithm can e.g. take the respective input image or a processed version of the input image, e.g. a lower resolution version generated by binning or a histogram, as input data and directly generate the necessary parameter or parameters and/or determine if the respective condition is fulfilled. Approaches for training such an algorithm will be discussed later.

As previously discussed, the image data of the first and/or second and/or third preparatory image can be determined by binning multiple detector elements or pixels to generate a superpixel. Alternatively, binning can be performed on the images themselves to reduce the resolution and at least some of the following processing steps can be performed using the resolution reduced images. When binning is used, the x-ray intensity or resulting grey values for multiple adjacent detector elements or pixels are added or averaged to generate a received intensity or a grey value for the superpixel. The binning can be performed directly by the x-ray detector, wherein the binning can be performed in the analogue domain, e.g. during the detector element readout, or in the digital domain once the detected values are digitized. Alternatively, the images can be provided at a higher resolution and the resolution can only be reduced by binning during the further processing.

To allow for the use of low x-ray doses, fast image acquisition, low transfer times and a low processing overhead, a binned detector mode can be used, wherein the x-ray detector can already bin arrays of neighbouring groups of e.g. two-by-two, three-by-three or four-by-four pixels or detector elements before transmitting a resolution reduced image for further processing.

Especially due to an applied binning, the resolution of the first and/or second and/or third preparatory image can be lower than the resolution of the image acquired during the main image acquisition.

The fulfilment of the and/or the further repeat condition and/or the main acquisition parameter and/or the first and/or the second and/or the third preparatory acquisition parameter and/or the segmentation of the first and/or the second and/or the third preparatory image can depend on an additional input image depicting the object, wherein the additional input image is an image acquired by an optical camera or an infrared camera or a THz-camera, and/or on prior knowledge concerning the object. The additional input image, prior knowledge and/or data generated by processing the additional input image and/or the prior knowledge can be used as additional input of an algorithm determining the fulfilment of the mentioned conditions and/or parameters and/or the segmentation. This can especially be advantageous when the algorithm is trained by machine learning, since the use of such additional inputs can noticeably improve the training process. When classical algorithms, lookup tables or similar approaches are used, it can e.g. be advantageous to use several different algorithms or lookup tables and select the used algorithm and/or lookup table based on the additional input image and/or the prior knowledge. Alternatively or additionally another input parameter can be added to the algorithm and/or another dimension can be added to the lookup table for taking the additional information into account.

The prior knowledge can e.g. concern the weight of the object, e.g. a weight of a patient, the depicted area, e.g. a depicted organ, information concerning prior operations on the patient, e.g. presence of artificial objects, especially metal, in the relevant region, etc. Such prior knowledge can e.g. be used to choose one of several algorithms used in a certain determination and/or to further parametrise the algorithms. Additionally or alternatively the prior knowledge can comprise knowledge concerning at least one prior image acquisition, especially a prior acquisition of an x-ray image. The prior knowledge can e.g. comprise at least one acquisition parameter used in a prior image acquisition to control an x-ray emitter and/or the resulting image and/or information concerning an image quality of the resulting image.

The use of an additional input image can e.g. be used to determine a contour of the object, e.g. of the body of a patient. A possible approach for determining a body contour and further information from additional images is e.g. discussed in the document WO 2018/035814 A1, the entire contents of which are hereby incorporated herein by reference. Well known approaches for image processing, e.g. a segmentation based on edge detection, can be used to extract a contour within the image plane. Using prior knowledge or additional images a three-dimensional body contour can be extracted.

Optical and/or infrared cameras are often present in medical imaging devices or can be added for a low cost. Such images are typically already sufficient to gather rough information concerning the position of the limbs and/or the head of a patient, a rough size and/or weight estimate, etc. Since a patient might be at least partially covered by cloths, e.g. a sterile cover, while the imaging is performed, the use of a THz-camera can be advantageous, since such cameras can still depict body contours even if those are covered by cloths.

The main acquisition parameter and/or the second and/or the third preparatory acquisition parameter and/or the fulfilment of the and/or the further repeat condition can be determined using an algorithm trained by machine learning. While the training can be part of the computer-implemented method, advantageously a pretrained algorithm is used, such that only the use of the algorithm is part of the computer-implemented method. In general an algorithm trained by machine learning can mimic cognitive functions that humans associate with other human minds. In particular by training based on training data the trained algorithm can be able to adapt to new circumstances and to detect and extrapolate patterns.

In general parameters of the algorithm can be adapted by means of training. In particular, supervised training, semi-supervised training, unsupervised training, reinforcement learning and/or active learning can be used. Furthermore representation learning, also called feature learning, can be used. In particular parameters of the algorithm can be adapted iteratively by several steps of training.

In particular, the algorithm can include or comprise a neural network, a support vector machine, a decision tree and/or a Bayesian network. An algorithm can also be based on k-means clustering, Q-learning, genetic algorithms and/or association rules. In particular, a neural network can be a deep neural network, a convolutional neural network or a convolutional deep neural network. Furthermore a neural network can be an adversarial network, a deep adversarial network and/or a generative adversarial network.

The trained algorithm can use the first and/or second and/or third image data or a part of this image data or data derived from this data, e.g. histogram data for at least one of the preparatory images or part of at least one of the preparatory images, as input data. The previously mentioned prior knowledge and/or additional input image and/or data derived from the additional input image and/or the prior knowledge can be used as additional input data. The output of the trained algorithm can be the respective acquisition parameter or parameters and/or a decision, if the and/or the further repeat condition is fulfilled.

In an example the training can be based on supervised learning. Multiple training data sets can be provided, each comprising the previously described input data and desired values for the respective output data. The algorithm can be parametrised by a multitude of parameters. The parameters can e.g. be input weights of artificial neurons in an artificial neural network. Initial values for the parameters can e.g. be chosen at random. The algorithm with its initial parametrisation can then be applied to the input data for a subset of the training data sets. A cost function can then evaluate the difference between the output of the algorithm for input data provided by a specific training data set and the desired value for the output parameter or parameters given by this training data set. This cost function is then minimized by varying the parameters of the algorithm during the training. This can be achieved by well-known approaches to machine learning, e.g. a back propagation of error.

The desired values of the acquisition parameters that should be generated by the trained algorithm can e.g. be manually provided for each training data set. It is however also possible to supervise the normal selection of acquisition parameters and then either allow for a user feedback concerning the quality of the resulting image or automatically determined such a quality by calculating a quality measure, e.g. a signal difference to noise ratio, for the image. Acquisitions that achieve a good quality while using a low dose can then be selected to provide the training data sets.

Machine learning can also be used to reduce the necessary number of preparatory images necessary to robustly determine the main acquisition parameter or parameters in a given situation. It might be e.g. be necessary to use two or three preparatory images in certain image situations when a first parametrisation is used for the trained algorithm. The training can then e.g. be improved by training the algorithm using training data sets that comprise desired output values that are determined based on the second or third preparatory image of prior image acquisitions, while only providing the algorithm with the first or second preparatory image of these acquisitions as input data. In many cases the training can be improved to generate a similar quality of final results even when using a lower number of preparatory images for the determination of the main acquisition parameter or parameters.

As previously discussed, the training of the algorithm for determining the main acquisition parameter and/or the second and/or the third preparatory acquisition parameters and/or the fulfilment of the and/or the further repeat condition can be performed as a separate method. The invention therefore also concerns a method for training an algorithm usable to determine the main acquisition parameter and/or the second and/or the third preparatory acquisition parameter and/or the fulfilment of the and/or the further repeat condition in a computer-implemented method discussed above.

At least one embodiment of the invention also concerns a training system comprising a first training interface, configured for receiving input training data, e.g. the input data discussed above, a second interface, configured for receiving output training data, e.g. the desired values for the respective acquisition parameter or parameters discussed above, wherein the input training data is related to the output training data, a training computation unit, configured for training an algorithm based on the input training data and the output training data, and a third training interface, configured for providing the trained algorithm.

Additionally, at least one embodiment of the invention concerns a computer program comprising instructions which, when the programs is executed by a computer, cause the computer to carry out the training of the algorithm. At least one embodiment of the invention also concerns a computer-readable medium comprising the instructions of the previously discussed computer program.

At least one embodiment of the invention also concerns the trained algorithm or any parameter set that parametrises a given algorithm to provide such a trained algorithm. A trained algorithm and/or the parameter set can especially be provided by the previously discussed method for training the algorithm and/or by the previously discussed training system. Therefore the invention also concerns a computer-readably storage medium comprising such a parameter set or trained algorithm.

At least one embodiment of the invention also concerns a method for acquiring a main x-ray image during a main image acquisition that uses an x-ray emitter and an x-ray detector for imaging on object, especially a patient during a medical image acquisition,
wherein a first preparatory image is acquired by the x-ray detector using at least one first preparatory acquisition parameter to control the x-ray emitter,
wherein a second preparatory image is acquired by the x-ray detector using at least one second preparatory acquisition parameter to control the x-ray emitter, in all cases or when a repeat condition is fulfilled, and
wherein the main x-ray image is acquired using a main acquisition parameter that controls the x-ray emitter during the main image acquisition to determine a dose of x-rays to be emitted from the x-ray emitter during the main image acquisition,
wherein first image data of the first preparatory image is evaluated to determine if the repeat condition is fulfilled and/or to determine the main acquisition parameter and/or the second preparatory acquisition parameter, and wherein the main acquisition parameter is determined depending on second image data of the second preparatory image in all cases or when the repeat condition is fulfilled.

The discussed method for acquiring a main x-ray image can comprise the previously discussed computer-implemented method for determining at least one main acquisition parameter. Additionally or alternatively individual features that are discussed with respect to that a computer-implemented method can be transferred to the claimed method for acquiring a main x-ray image with the discussed advantages. It is especially possible to acquire any number of preparatory images as discussed above. It is e.g. possible to test the fulfilment of a repeat condition after the acquisition of each preparatory image and only acquire a further preparatory image, when the repeat condition is fulfilled. In other words, it is possible to only acquire preparatory images that are also processed during the determination of the main image parameter that was already discussed in detail above.

The temperature of a cathode of the x-ray emitter and/or the rotational speed of an anode of the x-ray emitter can be increased during the acquisition of the first and/or the second preparatory image and/or between the acquisition of the first and second preparatory image and/or between the acquisition of the second preparatory image and the main image acquisition. If a third preparatory image is used or multiple further preparatory images are used, as discussed above, the rotational speed and/or a temperature can alternatively or additionally be increased during the respective acquisition of this third or the respective further preparatory image and/or before and/or after this acquisition.

As previously discussed, this allows the acquisition of the first and/or the second and/or the third preparatory image and/or further preparatory images while the x-ray emitter is preparing for the main image acquisition by increasing the cathode temperature and/or the rotational speed of the anode. Therefore the acquisition of the preparatory image does not necessarily increase the time required to acquire the main image.

The first and second preparatory image or the first, second and third preparatory image or more than three preparatory images can be acquired within one second. Preferably these two or three images can be acquired within 650 ms. The image acquisition of the preparatory images can therefore be performed during the time that is typically necessary to prepare the x-ray emitter for the main image acquisition, e.g. for spinning up the anode and/or heating the cathode. A delay in the imaging workflow can therefore be avoided.

At least one additional parameter concerning the position of the x-ray emitter and/or the collimation of the emitted x-rays by a collimator can be determined based on the first and/or second image data, wherein the position of the x-ray emitter or the configuration of the collimator is adjusted based on this additional parameter. Additionally or alternatively a foreign object detection can be performed based on the first and/or second image data, wherein a warning message is output to a user if a foreign object is detected. In some cases, a misalignment of the x-ray emitter or a misconfiguration of the collimator or the presence of objects disturbing the imaging, e.g. jewellery containing metal, is only recognised after the image acquisition in normal x-ray acquisition. This typically requires a repetition of the complete image acquisition therefore causing an increase in the applied x-ray dose and a delay in the imaging workflow. It is therefore proposed to already detect and correct or warn about potential causes of image deterioration based on the image data of the first and/or second preparatory image. If one of the discussed features is therefore detected it is only necessary to repeat the preparatory imaging, which needs noticeably lower x-ray dose and time than the full imaging.

At least part of the first and/or second image data or data derived from this image data can be processed by an algorithm, especially by an algorithm trained by machine learning, to determine a feature of the object. Obviously image data from further preparatory images, e.g. the third preparatory image, can be used in addition or as an alternative. General concepts about machine learning and the training of such algorithms were already discussed previously. Preferably the algorithm is an algorithm that uses the image acquired during the main image acquisition or at least part of its image data as input data. By using at least part of the first and/or second image data as additional input data, additional information can be provided e.g. to increase the robustness of the feature determination. The determined feature can e.g. be a segmentation and/or classification of a certain feature in the image. This can e.g. serve to support medical personal performing a diagnosis. E.g. lesions can be detected and/or classified.

Besides the inventive methods, at least one embodiment of the invention also concerns a processing unit, especially a processing unit of a medical imaging device, configured to perform at least one of the methods according to at least one embodiment of the present invention.

Additionally, at least one embodiment of the invention concerns an imaging device, especially an imaging device for medical imaging, comprising such a processing unit. The imaging device can comprise the x-ray emitter and the x-ray detector and the processing unit can optionally be configured to control the imaging. The processing unit can especially be configured to control the main image acquisition according to the at least one main acquisition parameter, to control the acquisition of the first preparatory image according to the at least one first preparatory acquisition parameter and/or to control the acquisition of the second preparatory image according to the at least one second preparatory acquisition parameter.

Alternatively the processing unit could be a device separate from any imaging device. It could e.g. be a local workstation or server, a server connected over a network or be implemented as a distributed solution, e.g. in a cloud.

The necessary calculations to perform the computer-implemented method according to at least one embodiment of the present invention can at least partially be performed in the detector hardware of the x-ray detector. Especially the binning of several pixels to a superpixel and/or the determination of at least one grey value and/or the histogram generation and/or the calculation of the signal difference to noise ratio can be performed in the detector hardware to reduce the required data transfer and therefore potentially a speed up the image acquisition.

At least one embodiment of the invention also concerns a computer program that can be directly loaded into a memory unit of a processing unit, especially a processing unit of a medical imaging device, the computer program comprising instructions for performing the steps of at least of the methods according to at least one embodiment of the present invention when the program is executed in the processing unit.

At least one embodiment of the invention also concerns a computer-readable storage medium containing electronically readable instructions comprising the computer program according to at least one embodiment of the present invention.

In the present application, the solution to the initially mentioned problem was discussed with respect to the processing unit as well as with respect to the methods. Features, advantages or alternative embodiments herein can be assigned to the other claimed objects and vice versa. In other words, claims for the processing unit can be improved with features described or claimed in the context of the methods and vice versa. In this case, the functional features of the method are embodied by objective units of the processing unit.

Additionally, as far as algorithms trained by machine learning are concerned, inventive features are discussed in the context of methods and systems that utilise the trained algorithm as well as in the context of methods and systems for training such algorithms. Features, advantages or alternative embodiments herein can be assigned to the other claimed objects and vice versa. In other words, claims for methods and systems for training the algorithm can be improved with features described or claimed in the context of methods and systems for utilising the trained algorithm and vice versa.

As far as input and/or output data of trained algorithms are discussed, features and advantages concerning input and output data used during the training of the algorithm can also be advantageously transferred to the input and output data of the trained algorithm when used in the inventive methods and vice versa.

FIG. 1 shows a flow chart of a computer-implemented method for determining at least one main acquisition parameter determining a dose of x-rays to be emitted from an x-ray emitter during a main image acquisition that uses the x-ray emitter and an x-ray detector for depicting an object, especially a patient during a medical image acquisition. The flow chart will be discussed in conjunction with FIG. 2 that shows selected relevant used data structures and algorithms in an example embodiment of this method.

In step S1 first image data of a first preparatory image 1 is received. The preparatory image 1 is an image that was acquired by the same x-ray detector that is used during the main image acquisition. The acquisition of the first preparatory image was preferably performed using a low x-ray dose. This can be achieved by using at least one first preparatory acquisition parameter to control the x-ray emitter associated with the x-ray detector during the image acquisition. The preparatory acquisition parameter can e.g. define the emitter voltage and/or current for the emitter, e.g. an x-ray tube, the used exposure time or an emitter charge that can be defined as the product of the emitter current and the exposure time when a constant current is used during the acquisition.

The image data of the first preparatory image can e.g. be read from a data base. Preferably however, the image data is provided directly from the detector, which can be advantageous when the discussed computer-implemented method is used to determine the main acquisition parameter in quasi-real time during the preparation of the acquisition.

In step S2, the first image data of the first preparatory image 1 is evaluated to determine if a repeat condition is fulfilled. If this is not the case, the image quality of the first preparatory image 1 is sufficient to immediately determine the main acquisition parameter from the first image data in step S3.

The evaluation of the first image data can be performed in a variety of ways. For simplicity's sake an evaluation using fixed or user-defined segments and grey values for these segments will be discussed with reference to FIG. 2. In this approach a segmented image 3 is generated by a segmentation algorithm 2. In the segmented image 3 a multitude of segments 4-8 are segmented. The positions and the sizes of the segments 4-8 in the segmented image 3 can be fixed or defined by a user. It would however also be possible to perform a segmentation based on the image data of the image 1 itself. E.g. bones, organs or other regions of interest could be segmented.

For each of the segments 4-8 a respective grey value 9-13 is determined, e.g. by averaging the grey values within the respective segment 4-8 or by choosing the median grey value from these grey values. An algorithm 14 then decides, if the grey values 9-13 indicate a sufficient image quality of the image 1 to allow for an immediate determination of the main acquisition parameter 15 based on the grey values 9-13 in step S3 or if the repeat condition is fulfilled and it will therefore be necessary to evaluate second image data of a second preparatory image 16 in step S4.

The algorithm 14 can e.g. be a lookup table or define a functional relationship between input and output values. In the simplest case only one of the grey values 9-13 is actually used. In a first step, the algorithm can e.g. choose the highest or a median grey value from the grey values 9-13. If the chosen grey value lies below a threshold, it can be assumed that the dose used to acquire the first preparatory image was too low and therefore the second preparatory image 16 needs to be considered. If this is not the case, the main acquisition parameter can e.g. be proportional to a quotient of a desired grey value and the chosen grey value with a fixed proportionality factor.

While the discussed procedure is very efficient, offsets of the grey values can strongly influence the results. To reduce such an influence multiple pairs of the grey values 9-13 can be selected and the determination of the main acquisition parameter can e.g. be based on a difference of the values of at least one pair to eliminate the offset. In the simplest case, the main acquisition parameter, e.g. the used dose or emitter charge, can be proportional to a quotient of a desired value for this difference and the calculated difference.

While the discussed segmentation based approach for the evaluation of the first image data allows for the use of a multitude of existing algorithms for segmenting an image, the main purpose of selecting the main acquisition parameter in such a way, e.g. to ensure that a certain contrast or signal difference to noise ratio is reached, can potentially be achieved without an explicit segmentation. A possible approach would be to calculate a histogram for the first image data. Especially when a histogram is calculated, it might be advantageous to use a binning of the pixel values of the image data to reduce the image resolution of the first preparatory image 1. Once the histogram is generated, clusters of similar grey values can easily be determined and e.g. two of these clusters can be chosen to determine a contrast of the image. If the contrast is not sufficient to robustly determine the main acquisition parameter, the method can branch to step S4. Otherwise the main acquisition parameter can be determined based on the contrast in step S3.

Often it is not only desirable to reach a certain contrast for the main image acquisition, but to reach a certain contrast to noise or signal difference to noise ratio. It is therefore also possible, that the evaluation of the first image data involves the calculation of a signal difference to noise ratio for the first preparatory image 1 or a certain segment, e.g. a region of interest, of the first preparatory image 1. The decision, if the repeat condition is fulfilled and the determination of the main acquisition parameter, if this condition is not fulfilled, can then depend on the signal difference to noise ratio.

If the image quality of the first preparatory image 1 is determined to be not sufficient to allow for an immediate determination of the main acquisition parameter 15 and when therefore the repeat condition is fulfilled in step S2, second image data of a second preparatory image 16 is received in step S4. As already discussed with respect to the first preparatory image 1, the second preparatory image 16 can be pre-acquired and e.g. be read out from a data base. It can however be advantageous to directly receive the second preparatory image 16 from the detector and especially to only acquire the second preparatory image 16 when the repeat condition is fulfilled in step S2. This avoids an additional exposure of the object to x-rays, if the main acquisition parameter can already be determined from the first preparatory image 1.

In step S5, the image data of the second preparatory image 16 is then evaluated to determine the main acquisition parameter 15. Different approaches for this evaluation were already discussed for the determination of the main acquisition parameter 15 from first preparatory image 1 and will therefore not be repeated.

The second preparatory image 16 especially is an image acquired using a higher dose or emitter charge than the first preparatory image 1. This can be achieved by using a longer exposure time and/or a higher emitter current. Additionally, or alternatively, a higher emitter voltage can be used to e.g. increase the contrast of the image.

It is e.g. possible to use a low x-ray emitter voltage of e.g. 40 kV and a low emitter current of e.g. 10 mA for the acquisition of the first preparatory image 1. Even when using a relatively long exposure time of e.g. 10 ms to 50 ms, a relatively low emitter charge and therefore dose of x-rays will result.

When relatively low emitter currents are used, the image acquisition is already possible when the cathode of the emitter is not yet fully heated. The relatively low emitter voltage and current also allow for an image acquisition, while the anode is standing still or rotating at a relatively low speed. Therefore the preparatory images can e.g. be acquired while the emitter, e.g. an x-ray tube, is prepared for the main image acquisition.

The second preparatory image 16 can be acquired at a higher rotational speed of the anode and/or a higher temperature of the cathode, therefore allowing for the use of higher currents and voltages.

In a further modification of the discussed method the repeat condition can be evaluated and/or the determination of the main acquisition parameter from the first or second image data can be performed using an algorithm trained by machine learning. Potential algorithms that can be trained will be discussed later with reference to FIGS. 7 and 8. An example for training such an algorithm will later be discussed with reference to FIG. 4.

Figure 3:
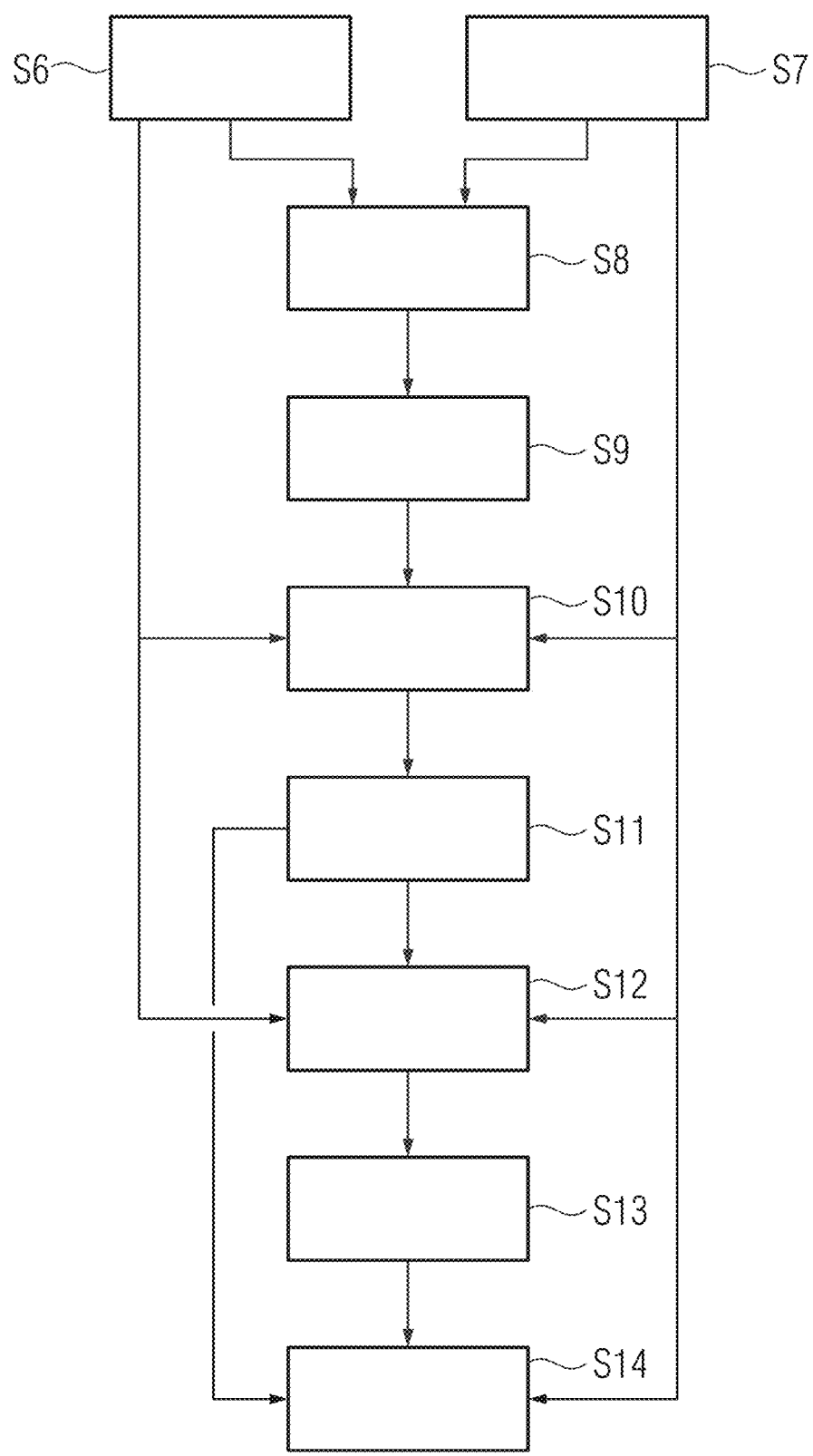
FIG. 3 shows a flow chart of an example embodiment of a method for acquiring a main x-ray image according to the present invention.

FIG. 3 shows a flow chart of a method for acquiring a main x-ray image during a main image acquisition that uses an x-ray emitter and an x-ray detector for imaging an object, especially a patient during a medical image acquisition. During the discussion of this method reference will be made to FIG. 5 that shows an example medical imaging device 17 that can be used to implement the discussed method and to FIG. 6 that shows a schematic detailed view of an x-ray emitter 18, e.g. an x-ray tube, used in the medical imaging device 17.

In step S6 prior knowledge concerning the patient or another depicted object 19 is acquired. Such information might e.g. be read out from a patient file and e.g. describe a weight of a patient, information which area should be imaged, information concerning prior operations and/or known artificial objects within the patient's body and/or images or other data, e.g. used imaging parameters from prior image acquisitions.

In step S7 an additional input image is acquired by the THz-camera 20. Alternatively, an optical or infrared camera could be used to acquire the additional input image. Preferably, the used camera is registered to the coordinate system of the x-ray detector 21 that is to be used to acquire the image during the main image acquisition. If such a registration is known or can be determined, the additional input image can e.g. facilitate the segmentation of acquired images.

In step S8, at least one first preparatory acquisition parameter is determined to control the x-ray emitter 18 during a first preparatory image acquisition. Various relevant first preparatory acquisition parameters where already discussed previously. E.g. an emitter charge might be varied based on a patient's weight provided by the prior knowledge and/or based on a body profile determined from the additional input image. Alternatively, fixed values could be used for the first preparatory acquisition parameter or parameters.

In step S9, a processing unit 23 of the medical imaging device 17 controls the x-ray emitter 18 according to the first preparatory acquisition parameter or parameters to acquire the first preparatory image 1 via the x-ray detector 21.

The processing unit 23 can be implemented by using a general-purpose processor 24 and an associated memory unit 25 by loading a computer program implementing the discussed functionality into the memory unit 25 and executing it by the processor 24. The processor 24 can be implemented in a variety of ways, e.g. as a general-purpose processor, micro controller, FPGA, etc. Alternatively, some or all of the discussed functionality could be hard-wired.

The processing unit 23 preferably also implements the steps concerning the processing of the various image data. For simplicity reasons, the processing unit 23 is shown as a compact unit that is integrated in a defined position within the imaging device 17. It might also be possible to distribute the processing throughout the imaging device 17, e.g. to perform at least part of the image processing in the detector 21 to limit the necessity of large data transfers during the relatively short time used to determine the main acquisition parameter. This is advantageous, since the determination of the main acquisition parameter including the acquisition of the preparatory images should be possible in less than one second, e.g. in 650 ms.

Figure 6:
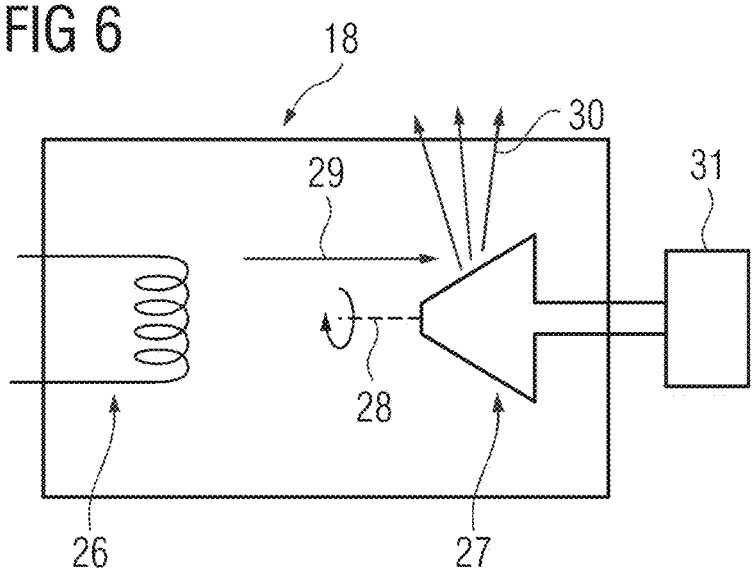
FIG. 6 shows a detailed view of an x-ray emitter used in the medical imaging device shown in FIG. 5, and FIGS. 7 and 8 show example structures of algorithm trained by machine learning that are useable in the embodiments of the methods according to the present invention.

The control of the x-ray emitter 18 will be discussed in detail with reference to FIG. 6 which shows an example x-ray emitter 18, e.g. an x-ray tube. The emitter voltage is applied between a cathode 26 and an anode 27 of the emitter 18 to accelerate electrons from the cathode 26 towards the anode 27 as shown by the arrow 29. When the fast electrons hit the anode 27 x-rays 30 are emitted. The spectrum of the emitted x-rays 30 depends on the speed of the electrons and therefore on the emitter voltage. For the acquisition of the first preparatory image 1 preferably relatively soft x-rays and therefore a relatively low emitter voltage of e.g. 40 kV are used. It is also advantageous to use a relatively low dose of x-rays for the fast-preparatory image 1, since a relatively long exposure time of 10 ms to 50 ms should be used, the dose can be limited by using a relatively low emitter current of e.g. 10 mA.

To prepare the x-ray emitter 18 for the main image acquisition, it is typically necessary to heat the cathode 26 to a certain temperature to allow for a sufficiently high emitter current. Since a relatively low emitter current is used for the acquisition of the first preparatory image 1, the acquisition of the first preparatory image can be performed at lower temperatures of the cathode 26, e.g. while still heating the cathode 26 for the main image acquisition.

In x-ray imaging it is possible to use relatively high emitter voltages and emitter currents for the main x-ray acquisition. Therefore, a relatively high power density is deposited by the accelerated electron at the position where these electrons hit the anode 27. It is therefore common to use a motor 31 to rotate the anode 27 around the axis 28, therefore changing the area of the anode 27 hit by the electrons over time. Typically, a few hundred ms are required to accelerate the anode 27 to the desired rotational speed. Since the first preparatory image 1 is recorded at relatively low emitter voltage and current, the first preparatory image can be acquired while the anode 27 is not yet rotating or rotating at a relatively low speed. It is especially possible to acquire the first preparatory image while the anode 27 is accelerating. This is another reason which allows for the acquisition of the first and the second preparatory images to be within a time frame which is required anyway to prepare the x-ray emitter 18 for the main image acquisition.

In step S10 the image data of the first preparatory image 1 is evaluated to determine second preparatory acquisition parameters that will be used to acquire a second preparatory image. While the quality of the first preparatory image is typically not sufficient to directly determine the main acquisition parameter or parameters, it can already be evaluated to determine the second preparatory acquisition parameter. Very low grey values, contrasts or signal difference to noise ratios in the first preparatory image might e.g. indicate, that a strong increase in exposure time, emitter current and/or emitter voltage should be used for the acquisition of the second preparatory image and vice versa. In principle, it would also be possible to check in step S10, if the image quality of the first preparatory image is sufficient to directly determine the main acquisition parameter from this image data. This was already discussed with reference to FIG. 2 and is not shown for reasons of clarity.

Figure 2:
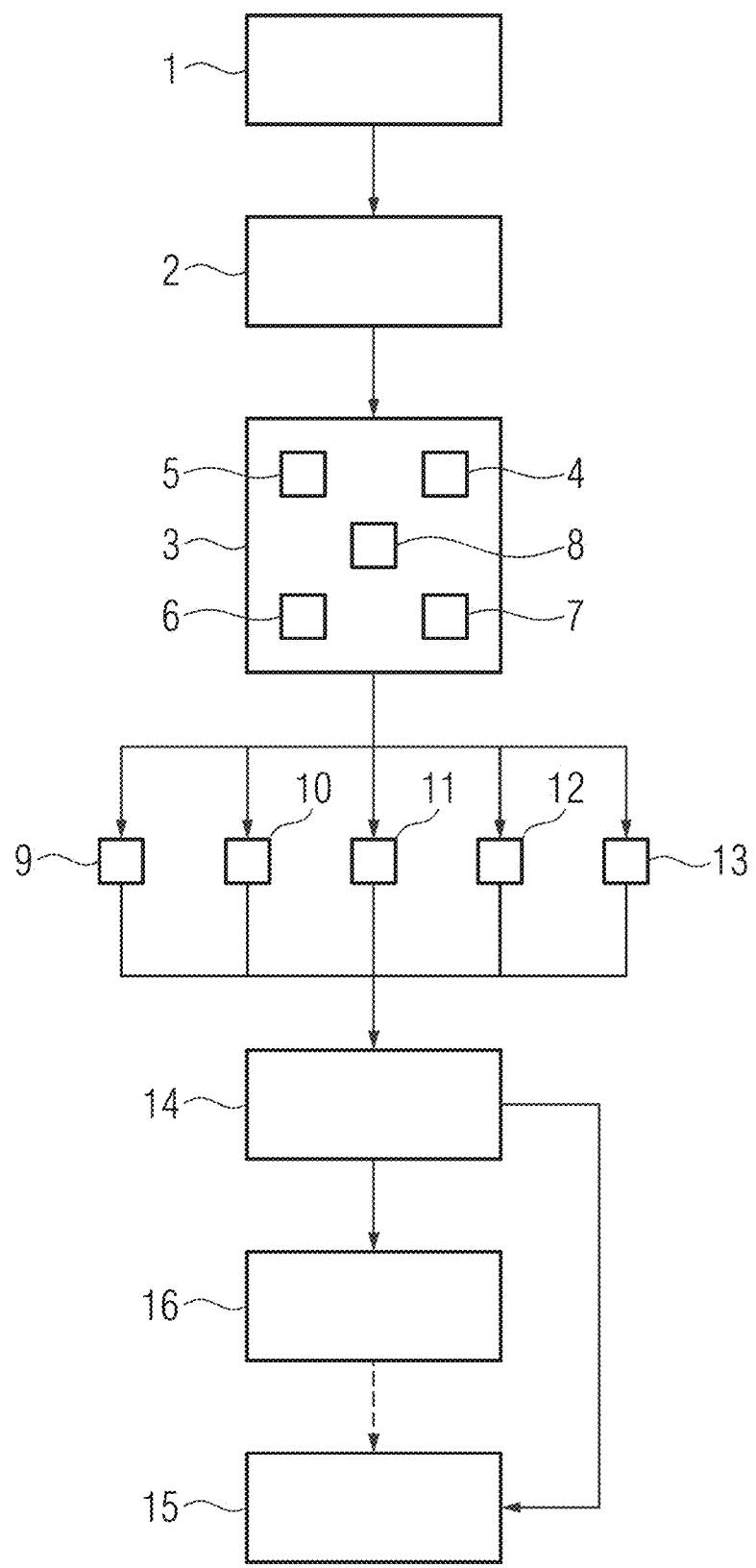
FIG. 2 shows selected relevant algorithms and data structures used in the computer-implemented method of FIG. 1.

The determination of the second preparatory acquisition parameter or parameters can be performed as already discussed with reference to FIG. 2 for the determination of the main acquisition parameter. The second preparatory acquisition parameters are typically chosen in such a way that the x-ray dose used during the acquisition of the second preparatory image is noticeably higher, e.g. ten times higher, than the dose used during the acquisition of the first preparatory image. It is however still noticeably lower than the dose used during the main image acquisition. If the preparatory images are acquired during the preparation of the x-ray emitter 18 for the main image acquisition, the temperature of the cathode 26 and/or the rotational speed of the anode 27 will typically be higher than for the acquisition of the first preparatory image. Therefore, it is easily possible to use higher emitter voltages and/or currents.

As shown in FIG. 3, the determination of the second preparatory acquisition parameter in step S10 can additionally depend on the prior knowledge provided in step S6 and/or the additional input image provided in step S7. This information can e.g. be used for segmenting regions of interest in the first preparatory image as already discussed with respect to FIG. 2. On the other hand, the use of this additional information is especially useful when the determination of the second preparatory acquisition parameter is performed by an algorithm trained by machine learning. Using additional input data can improve the convergence of the learning process and lead to more robust results.

In step S11 the second preparatory image is acquired by the x-ray detector 21 using the second preparatory acquisition parameter or parameters determined in step S10. The principles of this image acquisition were already discussed with respect to step S9.

The second image data of the second preparatory image 16 is then evaluated in step S12 in conjunction with the prior knowledge provided in step S6 and the additional input image provided in step S7 to determine the main acquisition parameter or parameters. Possible approaches for this determination were already discussed with respect to step S10 and FIG. 2.

In step S13 the main x-ray image is acquired using the main acquisition parameters that were determined in step S12 to control the x-ray emitter 18 during the main image acquisition. The main acquisition parameters therefore control the dose of the x-rays 30 to be emitted from the x-ray emitter 18 during the main image acquisition.

The acquired main x-ray image can then e.g. be processed to allow for automatic segmentation, classification of image segments, etc in Step S14. E.g. lesions can be segmented and/or classified. Several approaches for an automatic segmentation, classification, diagnosis assistance, etc. are well-known in the prior art and will not be discussed in detail.

To improve the robustness of the determined feature, additional information can be used. In the shown example, the additional input image determined in step S7 and the second preparatory image determined in step S11 are used as additional input data. Additionally, or alternatively, the prior knowledge determined in step S6 and/or the first preparatory image determined in step S9 could be used as additional input data.

Re-using the first and/or second preparatory image in this way can improve the quality of the results without increasing the x-ray dose used in the procedure. The algorithm used in step S14 can e.g. be trained by machine learning.

As previously discussed, several steps of the method for acquiring a main x-ray image and especially of the determination of the main acquisition parameter can be implemented by an algorithm trained by using machine learning. The algorithm can e.g. be a neural network, especially a convolutional neural network. The structure of such algorithms will later be discussed with reference to FIGS. 7 and 8.

Figure 4:
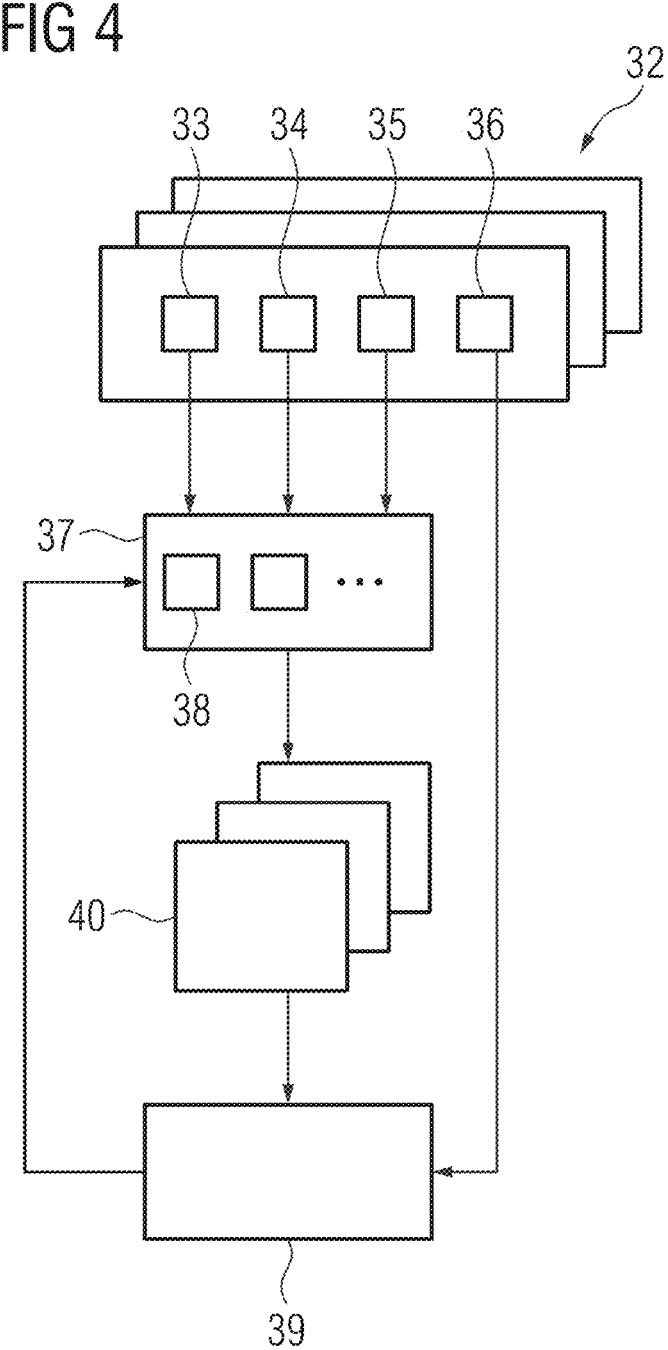
FIG. 4 shows an example embodiment of a method for training an algorithm useable in the methods according to the present invention by machine learning.

The training of such an algorithm will be explained using an example of supervised learning shown in FIG. 4. In this example, the algorithm 37 is trained to determine the at least one main acquisition parameter 40 based on the second image data 33 of the second preparatory image 16, the prior knowledge 34 and the additional input image 35. To lower the complexity of the algorithm 37 it can be advantageous to use binning for the second image data 33, combining multiple adjacent pixels into a super pixel and therefore reducing the image resolution, and/or to process a histogram of the second image data 33 instead of the second image data 33 itself.

The algorithm 37 has a multitude of parameters 38, e.g. input weights of the different nodes of a neural network. These parameters 38 can be set to initial values, e.g. standard values for the algorithm or random values.

A multitude of training data sets 32 are supplied, that each comprise second image data 33 or data derived from this data as discussed previously, the prior knowledge 34, the additional input image 35 and a desired value 36 for the at least one main acquisition parameter 40.

For a sub-set of the training data sets 32 the algorithm 37 is applied to the respective second image data 33, prior knowledge 34 and additional input image 35 to determine a respective value for the at least one main acquisition parameter 40. A cost function 39 is then minimized by varying the parameters 38. The cost function 39 is a sum of measures for the differences of the at least one main acquisition parameter 40 determined for the respective training data set 32 and the desired value 36 for the respective main acquisition parameter in this training data set 32. The variation of the parameters 38 can be e.g. be performed using the well-known back propagation of error approach. Several rounds of training can be performed with different sub-sets of the training data sets.

Figure 5:
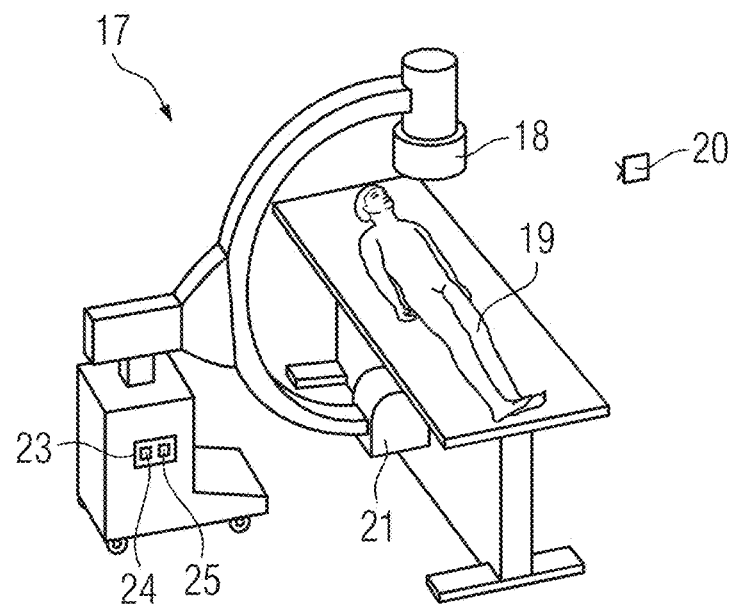
FIG. 5 shows an example embodiment of a medical imaging device that comprises an example embodiment of a processing unit according to the present invention.

Examples of algorithms that can be trained e.g. by the method discussed with reference to FIG. 5 will now be discussed in detail. For reasons of clarity only small neural networks with a few input nodes are shown. In real live applications, noticeably larger networks can be used.

Figure 7:
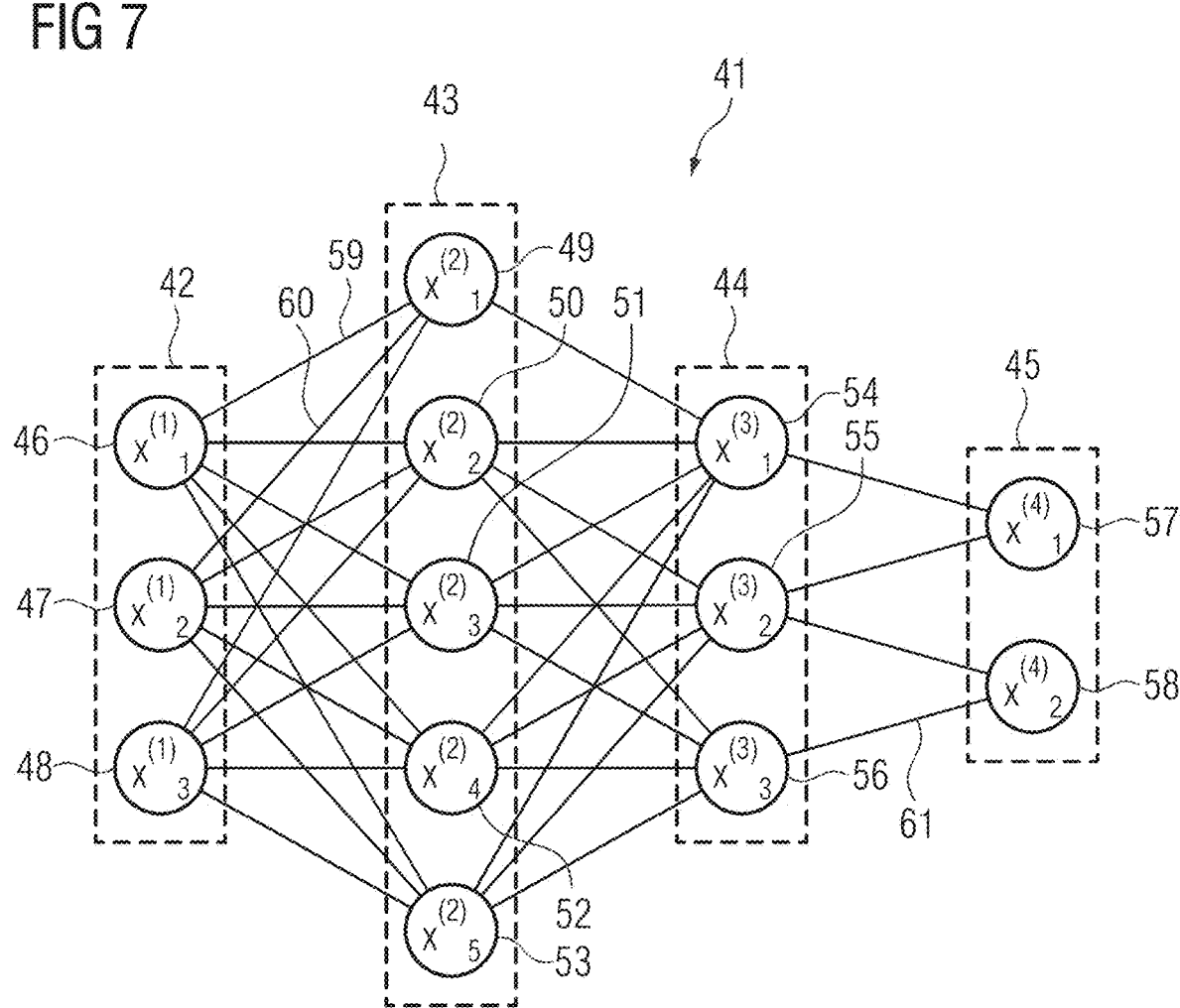

FIG. 7 displays an embodiment of an artificial neural network 41. Alternative terms for "artificial neural network" are "neural network", "artificial neural net" or "neural net".

The artificial neural network 41 comprises nodes 46-58 and edges 59-61 wherein each edge 59-61 is a directed connection from a first node 46-48 to a second node 46-58. In general, the first node 46-58 and the second node 46-58 are different nodes 46-58, it is also possible that the first node 46-58 and the second node 46-58 are identical. For example, in FIG. 1 the edge 59 is a directed connection from the node 46 to the node 49, and the edge 60 is a directed connection from the node 47 to the node 49. An edge 59-61 from a first node 46-58 to a second node 46-58 is also denoted as "ingoing edge" for the second node 46-58 and as "outgoing edge" for the first node 46-58.

In this embodiment, the nodes 46-58 of the artificial neural network 41 can be arranged in layers 42-45, wherein the layers 42-45 can comprise an intrinsic order introduced by the edges 59-61 between the nodes 46-58. In particular, edges 59-61 can exist only between neighboring layers of nodes 46-58. In the displayed embodiment, there is an input layer 42 comprising only nodes 46-48 without an incoming edge, an output layer 45 comprising only nodes 57, 58 without outgoing edges, and hidden layers 43, 44 in-between the input layer 42 and the output layer 45. In general, the number of hidden layers 43, 44 can be chosen arbitrarily. The number of nodes 46-48 within the input layer 42 usually relates to the number of input values of the neural network, and the number of nodes 57, 58 within the output layer 45 usually relates to the number of output values of the neural network.

In particular, a (real) number can be assigned as a value to every node 46-58 of the neural network 31. Here, $x^{(n)}_i$ denotes the value of the i-th node 46-58 of the n-th layer 42-45. The values of the nodes 46-48 of the input layer 42 are equivalent to the input values of the neural network 41, the values of the nodes 57, 58 of the output layer 45 are equivalent to the output value of the neural network 41. Furthermore, each edge 59-61 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 46-58 of the m-th layer 42-45 and the j-th node 46-58 of the n-th layer 42-45. Furthermore, the abbreviation $w^{(n)}_{i,j}$ is defined for the weight $w^{(n,n+1)}_{i,j}$.

In particular, to calculate the output values of the neural network 41, the input values are propagated through the neural network. In particular, the values of the nodes 46-58 of the (n+1)-th layer 42-45 can be calculated based on the values of the nodes 46-58 of the n-th layer 42-45 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smooth-step function) or rectifier functions. The transfer function is mainly used for normalization purposes.

In particular, the values are propagated layer-wise through the neural network, wherein values of the input layer 42 are given by the input of the neural network 41, wherein values of the first hidden layer 43 can be calculated based on the values of the input layer 42 of the neural network, wherein values of the second hidden layer 44 can be calculated based in the values of the first hidden layer 43, etc.

In order to set the values $w^{(m,n)}_{i,j}$ for the edges, the neural network 41 has to be trained using training data. In particular, training data comprises training input data and training output data (denoted as ti). For a training step, the neural network 41 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 41 (backpropagation algorithm). In particular, the weights are changed according to $$w'^{(n)}_{i,j} = w^{(n)}_{i,j} - \gamma \cdot \delta^{(n)}_j \cdot x_i^{(n)}$$

wherein $\gamma$ is a learning rate, and the numbers $\delta^{(n)}_j$ can be recursively calculated as $$\delta^{(n)}_j = (\Sigma_k \delta^{(n+1)}_k \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta^{(n)}_j = (x_k^{(n+1)} - t_j^{(n+1)}) \cdot f'(\Sigma_i x_i^{(n)} \cdot w_{i,j}^{(n)})$$

if the (n+1)-th layer is the output layer 45, wherein f' is the first derivative of the activation function, and $y^{(n+1)}_j$ is the comparison training value for the j-th node of the output layer 45.

FIG. 8 displays an embodiment of a convolutional neural network 62. In the displayed embodiment, the convolutional neural network 62 comprises an input layer 63, a convolutional layer 64, a pooling layer 65, a fully connected layer 66 and an output layer 67. Alternatively, the convolutional neural network 62 can comprise several convolutional layers 64, several pooling layers 65 and several fully connected layers 66 as well as other types of layers. The order of the layers can be chosen arbitrarily, usually fully connected layers 66 are used as the last layers before the output layer 67.

In particular, within a convolutional neural network 62 the nodes 68-72 of one layer 63-67 can be considered to be arranged as a d-dimensional matrix or as a d-dimensional image. In particular, in the two-dimensional case the value of the node 68-72 indexed with i and j in the n-th layer 63-67 can be denoted as $x^{(n)}[i,j]$. However, the arrangement of the nodes 68-72 of one layer 63-67 does not have an effect on the calculations executed within the convolutional neural network 62 as such, since these are given solely by the structure and the weights of the edges.

In particular, a convolutional layer 64 is characterized by the structure and the weights of the incoming edges forming a convolution operation based on a certain number of kernels. In particular, the structure and the weights of the incoming edges are chosen such that the values $x^{(n)}_k$ of the nodes 69 of the convolutional layer 64 are calculated as a convolution $x^{(n)}_k = K_k * x^{(n-1)}$ based on the values $x^{(n-1)}$ of the nodes 68 of the preceding layer 63, where the convolution is defined in the two-dimensional case as $$x_k^{(n)}[i,j] = (K_k * x^{(n-1)})[i,j] = \Sigma_{i'} \Sigma_{j'} [i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 68-72 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 68-72 in the respective layer 63-67. In particular, for a convolutional layer 64 the number of nodes 69 in the convolutional layer is equivalent to the number of nodes 68 in the preceding layer 63 multiplied with the number of kernels.

If the nodes 68 of the preceding layer 63 are arranged as a d-dimensional matrix, using a plurality of kernels can be interpreted as adding a further dimension (denoted as "depth" dimension), so that the nodes 69 of the convolutional layer 64 are arranged as a (d+1)-dimensional matrix. If the nodes 68 of the preceding layer 63 are already arranged as a (d+1)-dimensional matrix comprising a depth dimension, using a plurality of kernels can be interpreted as expanding along the depth dimension, so that the nodes 69 of the convolutional layer 64 are arranged also as a (d+1)-dimensional matrix, wherein the size of the (d+1)-dimensional matrix with respect to the depth dimension is by a factor of the number of kernels larger than in the preceding layer 63.

The advantage of using convolutional layers 64 is that spatially local correlation of the input data can exploited by enforcing a local connectivity pattern between nodes of adjacent layers, in particular by each node being connected to only a small region of the nodes of the preceding layer.

In the displayed embodiment, the input layer 63 comprises 36 nodes 68, arranged as a two-dimensional 6×6 matrix. The convolutional layer 64 comprises 72 nodes 69, arranged as two two-dimensional 6×6 matrices, each of the two matrices being the result of a convolution of the values of the input layer with a kernel. Equivalently, the nodes 69 of the convolutional layer 64 can be interpreted as arranges as a three-dimensional 6×6×2 matrix, wherein the last dimension is the depth dimension.

A pooling layer 65 can be characterized by the structure and the weights of the incoming edges and the activation function of its nodes 70 forming a pooling operation based on a non-linear pooling function f. For example, in the two dimensional case the values $x^{(n)}$ of the nodes 70 of the pooling layer 65 can be calculated based on the values $x^{(n-1)}$ of the nodes 69 of the preceding layer 64 as $$x^{(n)}[i,j]=f(x^{(n-1)}[id_1,jd_2],\ldots,x^{(n-1)}[id_1+d_1-1,jd_2+d_2-1])$$

In other words, by using a pooling layer 65 the number of nodes 69, 70 can be reduced, by replacing a number d1·d2 of neighboring nodes 69 in the preceding layer 64 with a single node 70 being calculated as a function of the values of said number of neighboring nodes in the pooling layer. In particular, the pooling function f can be the max-function, the average or the L2-Norm. In particular, for a pooling layer 65 the weights of the incoming edges are fixed and are not modified by training.

The advantage of using a pooling layer 65 is that the number of nodes 69, 70 and the number of parameters is reduced. This leads to the amount of computation in the network being reduced and to a control of overfitting.

In the displayed embodiment, the pooling layer 65 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 66 can be characterized by the fact that a majority, in particular, all edges between nodes 70 of the previous layer 65 and the nodes 71 of the fully-connected layer 66 are present, and wherein the weight of each of the edges can be adjusted individually.

In this embodiment, the nodes 70 of the preceding layer 65 of the fully-connected layer 66 are displayed both as two-dimensional matrices, and additionally as non-related nodes (indicated as a line of nodes, wherein the number of nodes was reduced for a better presentability). In this embodiment, the number of nodes 71 in the fully connected layer 66 is equal to the number of nodes 70 in the preceding layer 65. Alternatively, the number of nodes 70, 71 can differ.

Furthermore, in this embodiment the values of the nodes 72 of the output layer 67 are determined by applying the Softmax function onto the values of the nodes 71 of the preceding layer 66. By applying the Softmax function, the sum of the values of all nodes 72 of the output layer 67 is 1, and all values of all nodes 72 of the output layer 67 are real numbers between 0 and 1. In particular, if using the convolutional neural network 62 for categorizing input data, the values of the output layer can be interpreted as the probability of the input data falling into one of the different categories.

A convolutional neural network 200 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 62 can be trained based on the backpropagation algorithm. For preventing overfitting, methods of regularization can be used, e.g. dropout of nodes 68-72, stochastic pooling, use of artificial data, weight decay based on the L1 or the L2 norm, or max norm constraints.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for determining at least one main acquisition parameter determining a dose of x-rays to be emitted from an x-ray emitter during a main image acquisition using the x-ray emitter and an x-ray detector for imaging an object, the computer-implemented method comprising:
  evaluating first image data of a first preparatory image to at least one of
    determine whether or not a repeat condition is fulfilled,
    determine the at least one main acquisition parameter, and
    determine at least one second preparatory acquisition parameter, the first preparatory image being an image acquired by the x-ray detector using at least one first preparatory acquisition parameter to control the x-ray emitter;

determining, at least one of in all cases or only when the repeat condition is fulfilled, the at least one main acquisition parameter depending on second image data of a second preparatory image, acquired by the x-ray detector after the first preparatory image while the at least one second preparatory acquisition parameter is used to control the x-ray emitter; and evaluating the second image data to determine whether a further repeat condition is fulfilled;

wherein the at least one main acquisition parameter depends on third image data of a third preparatory image when the further repeat condition is fulfilled, the third preparatory image being an image acquired by the x-ray detector after the second preparatory image while at least one third preparatory acquisition parameter is used to control the x-ray emitter.

2. The computer-implemented method of claim 1, wherein the first preparatory image is an image acquired using, as the at least one first preparatory acquisition parameter, at least one of a first emitter voltage of less than 65 kV,
a first emitter current of less than 15 mA,
a first exposure time of less than 75 ms,
a first emitter charge of less than 750 µAs, or
a first rotational speed of an anode of the x-ray emitter of less than 10 Hz.

3. The computer-implemented method of claim 2, wherein the at least one first preparatory acquisition parameter, used during acquisition of the first preparatory image, describes at least one of
a first x-ray dose at least one of emitted from the x-ray emitter or absorbed by the object during the acquisition of the first preparatory image,
the first emitter voltage,
the first emitter current,
the first exposure time,
the first emitter charge, or
the first rotational speed of the anode of the x-ray emitter; and
wherein the at least one second preparatory acquisition parameter, used during acquisition of the second preparatory image, describes at least one of
a second x-ray dose at least one of emitted from the x-ray emitter or absorbed by the object during the acquisition of the second preparatory image,
a second emitter voltage,
a second emitter current,
a second exposure time,
a second emitter charge, or
a second rotational speed of the anode of the x-ray emitter
wherein the first preparatory image and the second preparatory image are images acquired such that at least one of
the second x-ray dose is larger than the first x-ray dose,
the second emitter voltage is larger than the first emitter voltage,
the second emitter current is larger than the first emitter current,
the second exposure time is larger than the first exposure time,
the second emitter charge is larger than the first emitter charge, or
the second rotational speed is larger than the first rotational speed.

4. The computer-implemented method of claim 2, wherein at least one of fulfilment of the repeat condition, the main acquisition parameter, or the at least one second preparatory acquisition parameter depend on at least one grey value determined from a respective segment of the first preparatory image, wherein a position of the respective segment in the first preparatory image is fixed or selected
by a user or determined by a segmentation algorithm,
on a histogram of the first image data or of part of the first image data, and
on a signal difference to noise ratio for the first image data or part of the first image data.

5. The computer-implemented method of claim 2, wherein at least one of the at least one main acquisition parameter, the at least one second preparatory acquisition parameter, the third preparatory acquisition parameter, or fulfilment of the repeat condition or the further repeat condition are determined using an algorithm trained by machine learning.

6. The computer-implemented method of claim 1, wherein the at least one first preparatory acquisition parameter, used during acquisition of the first preparatory image, describes at least one of
a first x-ray dose at least one of emitted from the x-ray emitter and absorbed by the object during the acquisition of the first preparatory image,
a first emitter voltage,
a first emitter current,
a first exposure time,
a first emitter charge, or
a first rotational speed of an anode of the x-ray emitter; and
wherein the at least one second preparatory acquisition parameter, used during acquisition of the second preparatory image, describes at least one of
a second x-ray dose at least one of emitted from the x-ray emitter and absorbed by the object during the acquisition of the second preparatory image,
a second emitter voltage,
a second emitter current,
a second exposure time,
a second emitter charge, or
a second rotational speed of the anode of the x-ray emitter
wherein the first preparatory image and the second preparatory image are images acquired such that at least one of
the second x-ray dose is larger than the first x-ray dose,
the second emitter voltage is larger than the first emitter voltage,
the second emitter current is larger than the first emitter current,
the second exposure time is larger than the first exposure time,
the second emitter charge is larger than the first emitter charge, or
the second rotational speed is larger than the first rotational speed.

7. The computer-implemented method of claim 1, wherein at least one of fulfilment of the repeat condition, the at least one main acquisition parameter, or the at least one second preparatory acquisition parameter depend on at least one grey value determined from a respective segment of the first preparatory image, wherein a position of the respective segment in the first preparatory image is fixed or selected
by a user or determined by a segmentation algorithm,
on a histogram of the first image data or of part of the first image data, and on a signal difference to noise ratio for the first image data or part of the first image data.

8. The computer-implemented method of claim 1, wherein at least one of fulfilment of at least one of the repeat condition or the further repeat condition, the at least one main acquisition parameter, the first preparatory acquisition parameter, the at least one second preparatory acquisition parameter, the third preparatory acquisition parameter, or segmentation of at least one of the first preparatory image, the second preparatory image or the third preparatory image, depend on an additional input image depicting the object, and wherein the additional input image is an image acquired by an optical camera, an infrared camera or a THz-camera.

9. The computer-implemented method of claim 1, wherein at least one of the at least one main acquisition parameter, the at least one second preparatory acquisition parameter, the third preparatory acquisition parameter, or fulfilment of the repeat condition or the further repeat condition are determined using an algorithm trained by machine learning.

10. A non-transitory computer readable medium storing a computer program, loaded into a memory unit of a processing unit of a medical imaging device, the computer program comprising instructions to configure the processing unit to perform the method of claim 1 when the computer program is executed on the processing unit.

11. A method for acquiring a main x-ray image during a main image acquisition using an x-ray emitter and an x-ray detector for imaging an object, the method comprising:
   acquiring a first preparatory image via the x-ray detector, using at least one first preparatory acquisition parameter to control the x-ray emitter;
   acquiring a second preparatory image via the x-ray detector, using at least one second preparatory acquisition parameter to control the x-ray emitter, at least one of in all cases or when a repeat condition is fulfilled;
   acquiring a third preparatory image via the x-ray detector, using at least one third preparatory acquisition parameter to control the x-ray emitter, the third preparatory image being acquired after the second preparatory image; and
   acquiring the main x-ray image using a main acquisition parameter that controls the x-ray emitter during the main image acquisition to determine a dose of x-rays to be emitted from the x-ray emitter during the main image acquisition;
   wherein first image data of the first preparatory image is evaluated at least one of to determine fulfilment of the repeat condition or to determine at least one of the main acquisition parameter or the at least one second preparatory acquisition parameter,
   wherein second image data of the second preparatory image is evaluated to determine whether a further repeat condition is fulfilled,
   wherein the main acquisition parameter depends on the second image data of the second preparatory image, at least one of in all cases or when the repeat condition is fulfilled, and
   wherein the main acquisition parameter depends on third image data of the third preparatory image when the further repeat condition is fulfilled.

12. The method of claim 11, further comprising at least one of:
   increasing at least one of a temperature of a cathode of the x-ray emitter or a rotational speed of an anode of the x-ray emitter at least one of
      during the acquiring of at least one of the first preparatory image or the second preparatory image,
      between the acquiring of the first preparatory image and the second preparatory image, or
      between the acquiring of the second preparatory image and the main image acquisition, or
   acquiring the first preparatory image and the second preparatory image or the first preparatory image, the second preparatory image and the third preparatory image within one second.

13. The method of claim 12, wherein at least one additional parameter concerning at least one of a position of the x-ray emitter or collimation on emitted x-rays by a collimator is determined based on at least one of the first image data or the second image data,
   wherein the position of the x-ray emitter or a configuration of the collimator is adjusted based on the at least one additional parameter,
   wherein foreign object detection is performed based on at least one of the first image data or the second image data, and
   wherein a warning message is output in response to detection of the foreign object.

14. The method of claim 11, wherein at least one additional parameter concerning at least one of a position of the x-ray emitter or collimation on emitted x-rays by a collimator is determined based on at least one of the first image data or the second image data,
   wherein the position of the x-ray emitter or a configuration of the collimator is adjusted based on the at least one additional parameter,
   wherein foreign object detection is performed based on at least one of the first image data or the second image data, and
   wherein a warning message is output in response to detection of the foreign object.

15. The method of claim 11, wherein at least part of the first image data and the second image data, or data derived from at least part of the first image data and the second image data, is processed by an algorithm trained by machine learning, to determine a feature of the object.

16. A non-transitory computer-readable storage medium storing electronically readable instructions to configure a processing unit to perform the method of claim 11.

17. A processing unit of a medical imaging device, configured to perform a computer-implemented method for determining at least one main acquisition parameter determining a dose of x-rays to be emitted from an x-ray emitter during a main image acquisition using the x-ray emitter and an x-ray detector for imaging an object, the computer-implemented method comprising:
   evaluating first image data of a first preparatory image to at least one of
      determine whether a repeat condition is fulfilled,
      determine the at least one main acquisition parameter, or
      determine at least one second preparatory acquisition parameter, the first preparatory image being an image acquired by the x-ray detector using at least one first preparatory acquisition parameter to control the x-ray emitter;
   determining, at least one of in all cases or only when the repeat condition is fulfilled, the main acquisition parameter depending on second image data of a second preparatory image, acquired by the x-ray detector after the first preparatory image while the at least one second preparatory acquisition parameter is used to control the x-ray emitter, and evaluating the second image data to determine whether a further repeat condition is fulfilled;

wherein the at least one main acquisition parameter depends on third image data of a third preparatory image when the further repeat condition is fulfilled, the third preparatory image being an image acquired by the x-ray detector after the second preparatory image while at least one third preparatory acquisition parameter is used to control the x-ray emitter.

18. An imaging device for medical imaging, comprising: the processing unit of claim 17.

* * * * *